(12) United States Patent
Wang et al.

(10) Patent No.: US 9,687,539 B2
(45) Date of Patent: Jun. 27, 2017

(54) CD4+ T SURVIVIN EPITOPES AND USES THEREOF

(71) Applicant: Commissariat a l'Energie Atomique, Paris (FR)

(72) Inventors: XiaoFei Wang, Paris (FR); Gaetan Munier, Orsay (FR); Sandra Moratille, Sainte Genevieve des Bois (FR); Helene Nuyttens, Paris (FR); Bernard Maillere, Versailles (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 14/510,550

(22) Filed: Oct. 9, 2014

(65) Prior Publication Data

US 2015/0050304 A1    Feb. 19, 2015

Related U.S. Application Data

(63) Continuation of application No. 12/088,602, filed as application No. PCT/FR2006/002196 on Sep. 28, 2006, now abandoned.

(30) Foreign Application Priority Data

Sep. 30, 2005  (FR) ..................... 05 10013

(51) Int. Cl.
| | |
|---|---|
| A61K 39/00 | (2006.01) |
| C07K 14/47 | (2006.01) |
| A61K 45/06 | (2006.01) |

(52) U.S. Cl.
CPC .......... *A61K 39/0011* (2013.01); *A61K 45/06* (2013.01); *C07K 14/4747* (2013.01); *A61K 39/00* (2013.01)

(58) Field of Classification Search
None
See application file for complete search history.

(56) References Cited

U.S. PATENT DOCUMENTS

| 5,840,839 A | 11/1998 | Wang et al. |
| 2007/0104689 A1* | 5/2007 | Gillies ............... A61K 39/0011 424/93.2 |

FOREIGN PATENT DOCUMENTS

| WO | 00/03693 A1 | 1/2000 |
| WO | 03/040299 A2 | 5/2003 |
| WO | 2004/055183 A2 | 7/2004 |
| WO | 2004/067023 A2 | 8/2004 |

OTHER PUBLICATIONS

Bachinsky et al, Cancer Immun, 5:6, 2005.*
Casati et al., "The Apoptosis Inhibitor Protein Survivin Induces Tumor-specific CD8+ and CD4+ T Cells in Colorectal Cancer Patients," Cancer Research, 63: 4507-4515 (2003).
Fortugno et al., "Survivin exists in immunochemically distinct subcellular pools and is involved in spindle microtubule function," Journal of Cell Science, 115: 575-585 (2002).
Byers, "What Can Randomized Controlled Trials Tell Us About Nutrition and Cancer Prevention?" CA Journal, 49: 353-361 (1999).
Ben-Efraim, "Once Hundred Years of Cancer Immunotherapy: A Critical Appraisal," Tumor Biology, 20: 1-24 (1999).
Granziero et al., "Adoptive immunotherapy prevents prostate cancer in a transgenic animal model," European Journal of Immunology, 29: 1127-1138 (1999).
Frazer, "Is vaccine therapy the future in cancer prevention?" Expert Opinion on Pharmacotherapy, 5: 2427-2434 (2004).
Wang et al., "Comprehensive Analysis of HLA-DR—and HLA-DP4-Restricted CD4 + T Cell Response Specific for the Tumor-Shared Antigen Survivin in Healthy Donors and Cancer Patients," The Journal of Immunology, 181: 431-439 (2008).
Stern et al., "Vaccination with Tumor Peptide in CpG Adjuvant Protects Via IFN-y-Dependent CD4 Cell Immunity," The Journal of Immunology, 168: 6099-6105 (2002).
Hung et al., "The Central Role of CD4+ T Cells in the Antitumor Immune Response," The Journal of Experimental Medicine, 188: 2357-2368 (1998).
Chicz et al., "Specificity and Promiscuity among Naturally Processed Peptides Bound to HLA-DR Alleles," The Journal of Experimental Medicine, 178: 27-47 (1993).
Schmitz et al., "Generation of Survivin-specific CD8+ T Effector Cells by Dendritic Cells Pulsed with Protein or Selected Peptides," Cancer Research, 60: 4845-4849 (2000).
Piesche et al., "Identification of a promiscuous HLA DR-restricted T-cell epitope derived from the inhibitor of apoptosis protein survivin," Human Immunology, 68: 572-576 (2007).
Piesche, "Doctorate Thesis: Identifikation und Iimmunologische Charakterisierung von MHC-Klasse-II-Peptidepitopen in humanen Leukamie-und Lymphom-assoziierten Antigenen," Abstract and pp. 67 and 86 (2006).

* cited by examiner

*Primary Examiner* — Mark Halvorson

(74) *Attorney, Agent, or Firm* — Morgan, Lewis & Bockius LLP

(57) ABSTRACT

The present invention concerns CD4+ T survivin epitopes and their vaccines and diagnostic uses.

15 Claims, 4 Drawing Sheets

CD4+ T SURVIVIN EPITOPES AND USES THEREOF

SEQUENCE LISTING SUBMISSION VIA EFS-WEB

A computer readable text file, entitled "045636-5091-01-SequenceListing.txt" created on or about Oct. 8, 2014, with a file size of about 10 kb contains the sequence listing for this application and is hereby incorporated by reference in its entirety.

The present invention relates to peptides representing CD4+ T epitopes of survivin that are able to be presented by HLA II molecules that are predominant, in particular in the Caucasian population, and to the vaccinal and diagnostic uses thereof.

Tumor antigens group together a collection of proteins expressed by tumor cells and that normal cells express relatively little or not at all, or which are found only in a few cell types. These antigens are divided up into five categories according to their expression profile: (1) antigens specific for the patient, resulting from point mutations related to tumorigenesis (MUM-1, CDK4, beta-catenin, HLA-A2, BCR-ABL, CASP-8), (2) tumor-specific antigens or CT (Cancer Testis) antigens, expressed in many tumors and a few normal tissues devoid of conventional HLA molecules (testicles, placenta, ovaries; MAGE, BAGE, GAGE, RAGE, NY-ESO1 antigens), (3) differentiation antigens which are expressed either during embryogenesis or in quite specific cell types (tyrosinases, gp-100, melan-A/mart-1, thyroglobulin, alpha-fetoprotein, CEA), (4) antigens overexpressed by tumors (survivin, gp75, PSA, HER-2/neu, p53, telomerase) and (5) viral antigens (EBV, HPV).

All these proteins which can be recognized by CD4+ and CD8+ T lymphocytes and can be used to induce an antitumor immunity represent targets for antitumor immunization (PCT international application WO 2004/055183).

The targets which have been particularly well studied are mainly tumor-specific antigens (MAGE, NY-ESO-1). However, these antigens may be ineffective targets for antitumor immunization, since most of them are not essential to the survival of tumor cells, which can evade immunological surveillance by decreasing or repressing the expression of these antigens.

Survivin (16.5 kDa), also called BIRC5 (Baculoviral IAP repeat-containing protein 5), IAP4 (inhibitor of apoptosis protein 4) or API4 (apoptosis inhibitor 4) is the smallest member of the family of apoptosis inhibitors (IAPB); it contains a zinc finger motif of 70 amino acids (BIR domain for Baculovirus inhibitor of apoptosis protein repeat), characteristic of all the members of the IAP family and a C-terminal end comprising a coiled-coil alpha-helix. The gene encoding survivin is located on human chromosome 17 (17q25) or murine chromosome 11 (11 E2); alternative splicing of a pre-mRNA comprising exons 1, 2, 2B, 3 and 4 produces three transcripts: (1) a transcript comprising exons 1, 2, 3 and 4, encoding the alpha-isoform of survivin (142 amino acids, GenBank AAC51660 or SwissProt O15392), (2) a transcript comprising exons 1, 2, 2B, 3 and 4, encoding the beta-isoform or survivin-2B (165 amino acids), which results from the insertion of the sequence IGPGTVAYACNTSTLGGRGGRITR (23 amino acids, SEQ ID No. 40), between positions 74 and 75 of the sequence of the alpha-isoform, and (3) a transcript comprising exons 1, 2 and 4, encoding survivin ΔEx-3.

Survivin is overexpressed in the majority of tumors, in particular in those associated with breast cancer, liver cancer, colon cancer, lung cancer, ovarian cancer, uterine cancer, esophageal cancer, stomach cancer, pancreatic cancer and prostate cancer, with Hodgkin's disease, with myelodysplastic syndrome with refractory anemia, and with melanomas, non-Hodgkin's lymphomas, leukemias, neuroblastomas, pheochromocytomas, soft tissue sarcomas and brain tumors. The overexpression of this nonredundant protein leads to an insensitivity to apoptosis and promotes cell division. In addition, this overexpression of survivin is essential to the survival of tumor cells; the extinction of survivin expression in human tumor cell lines by antisense methods or dominant-negative survivin mutants results in the arrest of cell division and apoptosis (Yang et al., P.N.A.S.; 2004, 101, 15100-15105; Altieri et al., Oncogene, 2003, 22, 8581-8589).

This tumor antigen is a good indicator of the prognosis of cancer; a high survivin level (mRNA) is correlated with an unfavorable prognosis (Takeuchi et al., Int. J. Cancer, 2005; Rodel et al., Cancer Res., 2005, 65, 4881-4887; Muzio et al., Cancer Lett., 2005, 225, 27-33; Kim et al., Cancer Lett., 2005, 224, 253-261).

On the other hand, survivin is virtually undetectable in differentiated normal tissues. It has a very short lifetime and is present only during mitosis, where it participates in the formation of the CPP (chromosomal passenger protein) complex which comprises the Aurora B kinase, the INCENP protein (inner centromere protein) and TD60 (telophase disk antigen), and is also involved in the inhibition of apoptosis by repressing the activity of caspases 3, 7 and 9 (Schimmer, A. D., Cancer Research, 2004, 64, 7183-7190; Fortugno et al., J. Cell. Science, 2002, 115, 575-585).

The study of the immune response directed against survivin, in individuals suffering from cancer, indicates that this tumor antigen can induce a cellular response involving specific CD4+ T lymphocytes and CD8+T lymphocytes (Anderson et al., Cancer Research, 2001, 61, 869-872 and 5964-5968; Schmidt et al., Blood, 2003, 102, 571-576; Casati et al., Cancer Research, 2003, 63, 4507-4515; Ichiki et al., Lung Cancer, 2005, 48, 281-289). Specific antibodies are also detected; the high anti-survivin antibody titer detected in cases of cancer with an unfavorable prognosis indicates, however, that the humoral response does not appear to be involved in the rejection of tumors expressing survivin (Ichiki et al., mentioned above).

Consequently, survivin represents a particularly advantageous target for antitumor immunization due to the fact that it induces a tumor-specific CD4+ and CD8+T response, that it is expressed in most tumors and that its expression is essential to tumor survival. In fact, the use of an antigen essential to tumor survival, as a target for antitumor immunization, makes it possible to avoid the problems of the tumors evading recognition by the immune system. In addition, most cancers can be treated with a single vaccine, due to the fact that survivin is expressed in the majority of tumors.

Thus, it has been proposed to use survivin (recombinant protein), an expression vector for this antigen or dendritic cells transfected with such an expression vector, as an antitumor vaccine (PCT international application WO 00/03693; Pisarev et al., Clin., Cancer Res., 2003, 9, 6523-6533; Siegel et al., J. Immunol., 2003, 170, 5391-5397; Schaft et al., J. Immunol., 2005, 174, 3087-3097). However, in order to induce both a CD4+ T response and a CD8+ T response that are effective against an antigen, it is preferable to use peptides representing the CD4+ T and CD8+ T epitopes of this antigen, rather than the whole protein.

Survivin CD8+ T epitopes restricted to the HLA-A1, A2, A3, A11, A24, B7, B8, B15 and B35 molecules of the major histocompatibility complex class I (HLA I or Human Leukocyte Antigen class 1 molecules) have been identified (HLA-A2-restricted peptides 95-104 and 96-104 (Andersen et al., Cancer Res., 2001, 61, 869-872; Schmitz et al., Cancer Res., 2000, 60, 4845-4849; Schmidt et al., 2003, mentioned above; PCT international application WO 2004/067023); HLA-A24-restricted survivin 2B peptide 80-88 (Hirohashi et al., Clin. Cancer Res., 2002, 8, 1731-1739); Recker et al., Int. J. Cancer 2004, 108, 937-941 and Cancer Biol. Ther., 2004, 3, 173-179; Bachinsky et al., Cancer Immun., 2005, 5, 6). Autologous dendritic cells loaded with the peptide 96-104 have been used to realize patients suffering from melanoma (Andersen et al., Vaccine, 2005, 23, 884-889).

However, immunization with CD8+ T epitopes alone induces tumor-antigen-specific cytotoxic T lymphocytes with a very low frequency (of the order of $10^{-4}$ to $10^{-7}$ of the CD8+ cells; Zhang et al., Eur. J. Immunol., 2005, 35, 776-785). In fact, the induction of cytotoxic T lymphocytes (CTLs) is dependent on the activation of the CD4+ T lymphocytes which are involved in particular in the recruitment and maintenance of the CTLs. It has been shown that CD4+ T lymphocytes play an essential role in the control of tumors. Through cell contacts and the secretion of numerous cytokines, CD4+ T lymphocytes induce the activation of antigen-presenting cells (APCs) which, in turn, recruit tumor-specific CD8+ T lymphocytes. They are also involved in the maturation of the effector cells, namely the cytotoxic T lymphocytes. In addition, the results observed in mice that do not express major histocompatibility complex class I molecules also indicate that CD4+ T lymphocytes exert a control over tumors via CTL-independent mechanisms, probably via macrophage activation. Finally, CD4+ T lymphocytes can themselves be cytotoxic.

CD4+ T lymphocytes recognize the tumor peptides presented to them by the major histocompatibility complex class II molecules; in humans, they are called HLA II molecules, for Human Leukocyte Antigen class II molecules. The recognition may take place directly (i.e. the tumor itself presents these peptides to the T lymphocytes), but it is probable that the principal activation pathway takes place via dendritic cells. These cells are in fact the main antigen-presenting cells capable of recruiting naïve T lymphocytes in vivo. These antigenic peptides, called T epitopes, result from the proteolytic degradation of the antigens by the antigen-presenting cells. They have varying lengths, generally from 13 to 25 amino acids, and have a sequence which makes them capable of binding to the HLA II molecules. It is well known that, just as the native antigen, a peptide comprising a CD4+ T epitope is capable of stimulating, in vitro, CD4+ T cells which are specific for it, or of recruiting them in vivo. It is therefore sufficient to induce a CD4+ T response.

These observations are in favor of the use of such survivin-specific antigenic peptides capable of stimulating a strong CD4+ T response, for the preparation of an antitumor vaccinal composition in humans, in particular in combination with CD8+ T epitopes specific for the same antigen.

In addition, such peptides which are recognized by CD4+T lymphocytes specific for a tumor antigen are also useful as reagents in a diagnostic test, a test for evaluating the prognosis or a test for monitoring the treatment of a cancer in humans, based on the detection of said CD4+ T cells, either directly, in particular by flow cytometry in the presence of multimers of class II molecule/peptide complexes, or indirectly, in particular by means of a lymphocyte proliferation assay, or else an antibody or cytokine assay.

However, no survivin CD4+ T epitope has been identified. In fact, one of the major problems that limits the use of these peptides as antigen is the identification of the CD4+ T epitopes, given that their sequence varies from one individual to the other due to the polymorphism of the HLA II molecules. HLA II molecules are heterodimers consisting of a polymorphic alpha-chain ($\alpha$) and a polymorphic beta-chain ($\beta$). Four types of HLA II molecules exist per individual (2 HLA-DR, 1 HLA-DQ and 1 HLA-DP), named according to the allele encoding the beta-chain which is the most polymorphic. The HLA-DR molecule is highly polymorphic. In fact, although its alpha-chain has only 3 alleles, the beta-chain ($\beta$) encoded by the DRB1 gene, which is the most widely expressed, to date has 458 alleles. For the HLA-DQ and HLA-DP molecules, the two chains ($\alpha$ and $\beta$) of which they are formed are polymorphic but they have fewer alleles. 28 DQA1 alleles ($\alpha$-chain of HLA-DQ), 60 DQB1 alleles ($\beta$-chain of HLA-DQ), 22 DPA1 alleles ($\alpha$-chain of HLA-DP) and 116 DPB1 alleles ($\beta$-chain of HLA-DP) have been counted. However, the combination between the two $\alpha$- and $\beta$-chains encoded by these alleles gives rise to numerous HLA-DQ and HLA-DP molecules.

As a result of this polymorphism, these isoforms have binding properties different than one another, which implies that they can bind different peptides of the same antigen. Thus, the method of binding of the peptides to the HLA II molecules is more complex than that of the HLA I molecules, and no reliable programs exist for predicting the peptides capable of binding to HLA II molecules. In fact, the HLA molecules have a very similar three-dimensional structure, but the binding site of HLA II molecules is a groove open at the two ends. For this reason, the HLA II molecules accept HLA II molecule-restricted peptides of variable size, generally between 13 and 25 amino acids. This groove is characterized by five specificity pockets (P1, P4, P6, P7 and P9 corresponding to the positions of the residues of the peptide that they accommodate) which harbor polymorphic residues. Since the differences in sequences between the various HLA II molecules are essentially located in the pockets of the peptide-binding site, they are directly involved in the repertoire of peptides which bind to each molecule.

Thus, each individual recognizes in an antigen a set of peptides whose nature depends on the HLA II molecules which characterize it. Since there exists a large number of HLA II alleles, there therefore exists, in a given sequence, a large repertoire of T epitopes of very different sequences, each specific for a different allele. A peptide capable of stimulating a CD4+ T response specific for a tumor antigen in some individuals may therefore be inactive in the majority of other individuals, because the latter do not recognize the tumor antigen via the same epitopes.

However, the HLA II molecules do not appear to be used uniformly for tumor recognition. In fact, the T epitopes derived from tumor antigens are for the most part restricted to the HLA-DR molecules, suggesting that the HLA-DQ molecules are apparently only weakly used for tumor recognition.

In addition, the HLA II alleles are not distributed uniformly throughout the world. Thus, ten HLA-DR molecules are predominant in Europe and in the United States and cover most of the population; they are the molecules whose beta-chain is encoded by the seven alleles of the locus HLA-DRB1: *0101, *0301, *0401, *0701, *1101, *1301, *1501, and the alleles DRB3*0101, DRB4*0101 and DRB5*0101 (table I).

TABLE I

Gene (allelic*)/phenotypic frequency of HLA II

| Alleles | Europe | | USA | | Africa | Asia | |
|---|---|---|---|---|---|---|---|
| | France | Germany | Caucasian | Afro-American | Senegal | India | Japan |
| DRB1*0101 | 9.3/17.7 | 6.7/13 | 7.3/14.1 | 1.9/3.8 | 0.6/1.2 | 3.8/7.5 | 4.9/9.6 |
| DRB1*0401 | 5.6/10.9 | 8.1/15.5 | 6.7/13 | 1.5/3.0 | 0/0 | 0.9/1.8 | 0/0 |
| DRB1*1101 | 9.2/17.6 | 9.2/17.6 | 4.4/8.6 | 8.2/15.7 | 9.3/17.7 | 0.9/1.8 | 2/4 |
| DRB1*0701 | 14.0/26 | 12.3/23.1 | 14.4/26.7 | 9.8/18.6 | 7.8/15 | 13/24.3 | 0.6/1.2 |
| DRB1*0301 | 10.9/20.6 | 9.4/17.9 | 9.5/18.1 | 7/13.5 | 10.2/19.4 | 5.3/10.3 | 0.4/0.8 |
| DRB1*1301 | 6.0/11.6 | 4.5/8.8 | 5.1/9.9 | 4.2/8.2 | 4.7/9.2 | 6.3/12.2 | 0.7/1.4 |
| DRB1*1501 | 8.0/14.4 | 7.8/15 | 10.3/19.5 | 8.6/16.5 | 0/0 | 12.1/22.7 | 9.1/17.4 |
| TOTAL | 63.0/86.3 | 58.0/82.4 | 57.7/82.1 | 41.2/65.4 | 32/54.66 | 42.3/66.7 | 17.7/32.3 |
| DRB5*0101 | 7.9/15.2 | 4.6/9 | 2.4/4.7 | 10.4/19.7 | 0/0 | 0/0 | 5.6/10.9 |
| DRB3*0101 | 9.2/17.6 | 9.8/18.6 | 10.4/19.7 | 15.1/27.9 | 6.9/13.3 | 4.9/9.6 | 6.5/12.6 |
| DRB4*0101 | 28.0/48.2 | 21.1/37.7 | 19.8/35.7 | 16.5/30.3 | 6.9/13.3 | 24.8/43.4 | 28.9/49.4 |
| TOTAL | 45.1/69.9 | 35.5/58.4 | 32.6/54.6 | 42.0/66.4 | 13.8/25.7 | 29.7/50.6 | 41.0/65.2 |
| DPB1*0101 | 7.1/13.7 | 2.2/4.4 | 3.2/6.3 | 27.7/47.7 | 18.2/33.1 | nd | 0.1/0.2 |
| DPB1*0201 | 11.9/22.4 | 8.5/16.3 | 9.8/18.6 | 12.9/24.1 | 13.8/25.7 | nd | 20.6/37 |
| DPB1*0301 | 17.0/31.1 | 3.8/7.5 | 7.4/14.3 | 3.3/6.5 | 3.8/7.5 | nd | 3/5.9 |
| DPB1*0401 | 40.0/64 | 38.1/61.7 | 25.1/43.9 | 11/20.8 | 4.8/9.4 | nd | 4.7/9.2 |
| DPB1*0402 | 11.0/20.8 | 15.4/28.4 | 12.6/23.6 | 9/17.2 | 25.5/44.5 | nd | 36.8/60.1 |
| TOTAL | 87.0/98.3 | 68.0/89.8 | 58.1/82.4 | 63.9/87.0 | 66.1/88.5 | nd | 65.2/87.9 |
| Total DP401 + 402 | 51/76 | 53.5/78.4 | 37.7/61.2 | 20/36.0 | 30.3/51.4 | nd | 41.5/65.8 |

*The predominant HLA II molecules (gene frequency > 5%) are indicated in bold

For example, in the French population, which is a population characteristic of the Caucasian population (USA, Europe), only the 7 alleles of the DRB1 locus have an allelic frequency greater than 5%; these 7 DRB1 alleles represent by themselves 63% of the population. These same DRB1 alleles are the HLA-DR alleles that are the most abundant in the other Caucasian populations. Their frequency varies between 53% (in Spain) and 82% (in Denmark). For the United States and Canada, they represent 58% and 55%, respectively, of the alleles of the population.

In addition, some of the DRB1 alleles most frequent in the Caucasian population are also frequent in the African population (DRB1*0301, *0701 and *1101), the Indian population (DRB1*0301, *0701, *1301 and *1501) and the Japanese population (DRB1*1501).

The HLA-DRB3, -DRB4 and -DRB5 molecules, which are HLA-DR molecules whose β-chain is not encoded by the DRB1 gene, are also predominant in Europe, in the USA and in Japan, since they are less polymorphic than the DRB1 molecules (table I). For example, in France, their allelic frequency is 9.2% for DRB3*0101, 28% for DRB4*0101 and 7.9% for DRB5*0101. They therefore cover by themselves 45% of the allelic frequency in France.

Furthermore, the binding motifs of certain HLA-DR molecules are identical to such an extent that a peptide can bind to several HLA-DR molecules. In addition, it is not uncommon for CD4+ T epitopes to be interwoven in one another, to such an extent that a peptide sequence may contain several CD4+ T epitopes.

Finally, two HLA-DP4 molecules (DP401 and DP402) cover by themselves the majority of the allelic frequency of HLA-DP in the Caucasian population (of the order of 50% in Europe and 80% in North America) and are also present at not insignificant frequencies in the other populations (allelic frequency of the order of 60% in South America, 60% in India, 30% in Africa and 40% in Japan; table I). Each of these DP4 molecules comprises an alpha-chain encoded either by the DPA1*0103 allele, which is the most frequent (78.2%), or by the DPA1*0201 allele (20.2%), and a beta-chain encoded by the DPB1*0401 allele (HLA-DP401 molecule) or the DPB1*0402 allele (HLA-DP402 molecule).

Like the HLA-DR molecules, the HLA-DP4 molecules are entirely capable of presenting peptides to lymphocytes insofar as numerous HLA-DP4-restricted T clones have been isolated using very varied antigens such as tetanus toxin, hepatitis B virus and the *Dermatophagoides pteronyssimus* major allergen.

The peptides which bind the HLA II molecules encoded by the alleles that are most frequent in the population (predominant HLA II molecules) therefore include the T epitopes of the majority of the population.

The inventors have identified three regions of survivin containing CD4+ T epitopes restricted to the 12 HLA II molecules predominant in the Caucasian population. These peptides represent potential candidates for prophylactic or therapeutic immunization against cancers, given that they are capable of inducing a CD4+T response directed against the tumor, in the majority of patients immunized, since: (i) they are derived from an antigen expressed by the majority of tumor cells, (ii) they are capable of inducing CD4+ T lymphocytes specific for this antigen, and (iii) they take into account the polymorphism of the HLA II molecules.

In addition, these peptides, which are recognized by CD4+ T lymphocytes specific for a tumor antigen expressed by the majority of tumor cells, can be used for establishing the prognosis and monitoring the evolution of cancers.

Consequently, a subject of the present invention is a peptide derived from the alpha-isoform of survivin, for use as an antigen in the prophylactic or therapeutic immunization against cancer, or the diagnosis, prognosis or therapeutic monitoring of cancer, said peptide being selected from the group consisting of:

a) the peptides of 13 to 18 consecutive amino acids located between positions 17 and 34 of the alpha-isoform of survivin, b) the peptides of 13 to 30 consecutive amino acids located between positions 84 and 113 of the alpha-isoform of survivin, c) the peptides of 13 to 21 consecutive amino acids located between positions 122 and 142 of the alpha-isoform of survivin, and d) the variants of the peptides defined in a), b) or c), said peptides in a), b) or c), or variants in d), having a binding activity with respect to at least one HLA II molecule predominant in the Caucasian population, of less than 1000 nM, and being capable of inducing survivin-specific CD4+ T lymphocytes.

BRIEF DESCRIPTION OF DRAWINGS

In addition to the below arrangements, the invention also comprises other arrangements, which will emerge from the description which follows, which refers to examples of implementation of the subject of the present invention, with reference to the attached drawing in which.

DEFINITIONS

Figure 1:
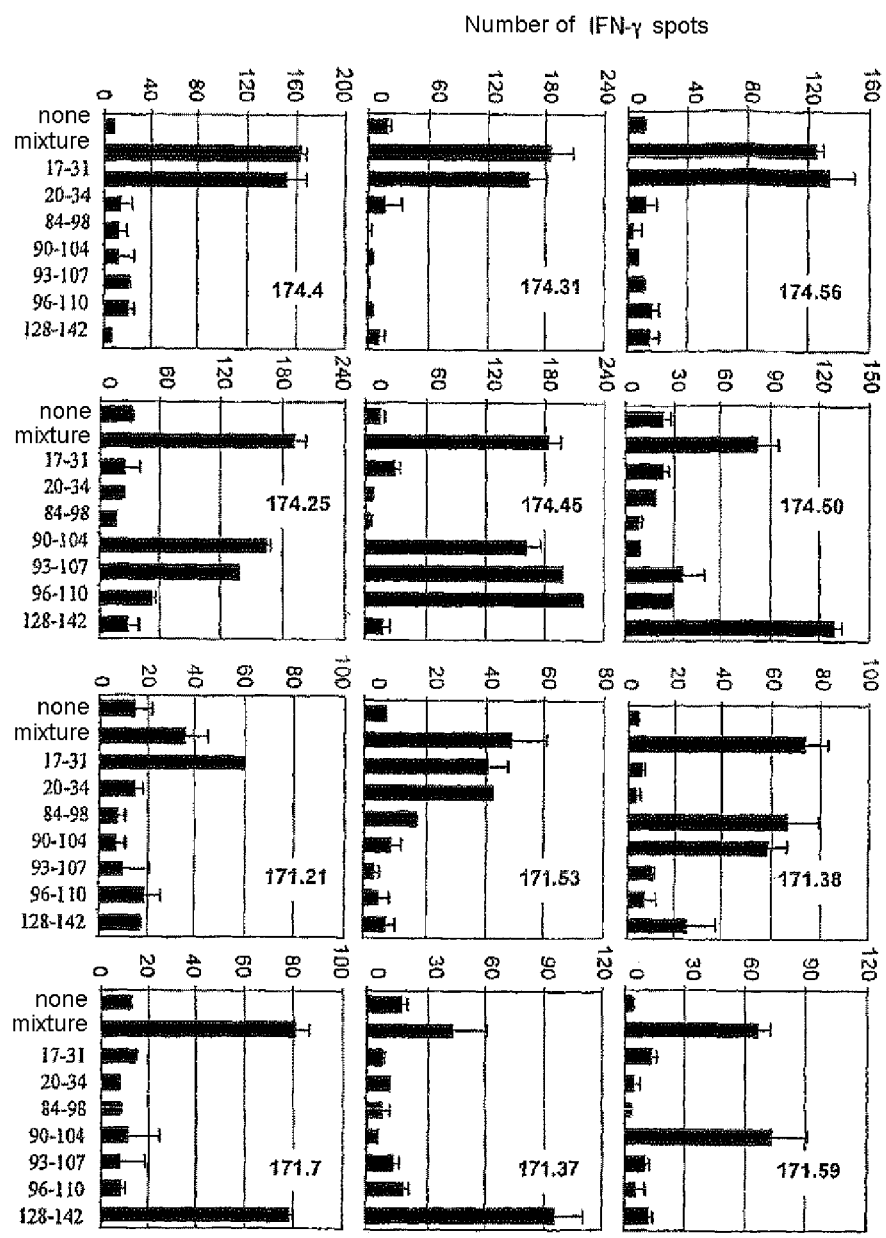
FIG. 1 illustrates the specificity of the CD4+ T lymphocyte lines obtained from the PBMCs of normal donors 171 and 174. The CD4+ T lymphocyte lines were obtained after three stimulations one week apart, with autologous dendritic cells loaded with a mixture of the seven peptides selected (17-31, 20-34, 84-98, 90-104, 93-107, 96-110 and 128-142). The specificity of the T lymphocyte lines was evaluated by IFN-γ ELISPOT. $10^4$ CD4+ T lymphocytes were incubated, in duplicate, with $10^5$ autologous PBMCs, in the presence or absence of peptide. The spots were revealed 24 h after the incubation. Each bar represents the mean number of spots of the duplicates±the standard deviation. The positive values are at least three times greater than those of the negative control.

The expression "peptide capable of being presented by at least one HLA II molecule" is intended to mean a peptide having a binding activity with respect to at least one HLA II molecule of less than 1000 nM.

The term "survivin" is intended to mean the three isoforms of survivin: alpha-isoform, survivin-2B and survivin ΔEx-3. These isoforms may be derived from any mammal; they are preferably human isoforms. The alpha-isoform of survivin corresponds to the survivin of 142 amino acids; the positions are indicated with reference to the human sequence (Genbank AAC51660 or SwissProt O15392).

The expression "HLA II molecule predominant in the Caucasian population" or "predominant HLA II molecule" is intended to mean an HLA II molecule comprising a beta-chain encoded by an allele whose frequency is greater than 5% in the Caucasian population, as specified in table I above. Some of the HLA II molecules predominant in the Caucasian population, and in particular the HLA-DP401 and HLA-DP402 molecules, are also predominant in other populations (South America, India, Japan, Africa; table I). Consequently, the peptides according to the invention are not restricted to use in the Caucasian population, and they may also be used to immunize individuals of countries other than those of North America and Europe, in which said HLA II molecules are predominant, as specified in table I.

The term "cancer" is intended to mean a cancer associated with the overexpression of survivin, such as, in a nonlimiting manner: breast cancer, liver cancer, colon cancer, lung cancer, ovarian cancer, uterine cancer, esophageal cancer, stomach cancer, pancreatic cancer and prostate cancer, melanomas, Hodgkin's disease, non-Hodgkin's lymphomas, leukemias, myelodysplastic syndrome with refractory anemia, neuroblastomas, pheochromocytomas, soft tissue sarcomas and brain tumors.

The peptides according to the invention comprise a survivin CD4+ T epitope capable of being presented to at least one predominant HLA II molecule, which epitope consists of a sequence of 9 amino acids including the residues for anchoring to the HLA II molecules, flanked at one of its ends, preferably at both ends, by at least 2 amino acids, preferably 3 amino acids.

The peptides according to the invention have the following properties:

HLA II molecule-binding activity: the peptides according to the invention have good affinity for the predominant HLA II molecules, in particular predominant in the Caucasian population (binding activity <1000 nM); the binding activity can be measured by means of a competitive HLA II/peptide binding assay, with immunoenzymatic visualization, according to the principle described in U.S. Pat. No. 6,649,166 and PCT international application WO 03/040299, for the HLA-DR and HLA-DP4 molecules, respectively;

immunogenicity: these peptides are also capable of inducing survivin-specific CD4+ T cells from the precursors present in the majority of naïve individuals, or else of stimulating such cells in the majority of individuals suffering from a cancer associated with the overexpression of survivin. The immunogenicity of the peptides can be determined, in particular using peripheral blood mononuclear cells (PBMCs), by means of any appropriate assay known to those skilled in the art, such as, for example: a cell proliferation assay, an ELISPOT assay (assaying of cytokine-producing cells) or a test for assaying intracellular cytokines (INF-γ, IL-2, IL-4 and IL-10).

The invention encompasses the natural or synthetic variants obtained by mutation (insertion, deletion, substitution) of one or more amino acids in the sequence of the alpha-isoform of human survivin, provided that said variant conserves a good affinity for at least one predominant HLA II molecule, in particular predominant in the Caucasian population (binding activity <1000 nM), and is immunogenic. The natural variants result in particular from the polymorphism of survivin. In addition, other variants may be readily constructed, given that the amino acid residues involved in the binding to the HLA-DR and HLA-DP4 molecules (anchoring residues) and the effect of modifications of these residues on the binding to the HLA-DR and HLA-DP4 molecules are known to those skilled in the art; PCT international application WO 03/040299 teaches in particular that in order to bind HLA-DP4, the residue at P6 must be aromatic or hydrophobic or consist of a cysteine residue (C), and at least one of the residues P1 and P9 is such that P1 is aromatic or hydrophobic and/or P9 is aromatic or hydrophobic or consists of a residue C, D, Q, S, T or E, whereas the residue at P4 may be any amino acid residue. U.S. Pat. No. 6,649,166 describes a general method for determining the residues for anchoring to the HLA DR molecules (P1, P4, P6, P7 and P9) and the nature of the mutations of these residues that make it possible to modify the affinity for the HLA DR molecules. HLA DR molecule-binding motifs are described in particular in Sturnolio et al., Nat. Biotech, 1999, 17, 533-534 and Rammensee et al., Immunogenetics, 1995, 41, 178-228.

The invention also encompasses the modified peptides derived from the previous peptides by introduction of any modification at the level of one or more amino acid residue(s), of the peptide bond or of the ends of the peptides, provided that said modified peptide conserves a good affinity for at least one predominant HLA II molecule, in particular predominant in the Caucasian population (binding activity <1000 nM), and is immunogenic. These modifications which are introduced into the peptides by conventional methods known to those skilled in the art include, in a nonlimiting manner: substitution of an amino acid with a non-protein-generating amino acid (D amino acid or amino acid analogue); addition of a chemical group (lipid, oligosaccharide or polysaccharide) at a reactive function, in particular the side chain R; modification of the peptide bond (—CO—NH—), in particular with a bond of the retro or retroinverso type (—NH—CO—) or a bond other than the peptide bond; cyclization; fusion of a peptide (epitope of interest for immunization; tag that can be used for purifying the peptide, in particular in a form cleavable by a protease); fusion of the sequence of said peptide with that of a protein, in particular an α- or β-chain of an HLA II molecule or the extracellular domain of said chain, or alternatively a sequence for targeting to the endosome, derived in particular from the Ii invariable chain or from the LAMP-1 protein; coupling to an appropriate molecule, in particular a label, for example a fluorochrome. These modifications are intended in particular to increase the stability, and more particularly the resistance to proteolysis, and also the solubility or the immunogenicity, or to facilitate the purification or the detection either of the peptide according to the invention or of CD4+ cells specific for said peptide.

According to an advantageous embodiment of said peptide, said HLA II molecule predominant in the Caucasian population is chosen from the HLA-DR1, HLA-DR3, HLA-DR4, HLA-DR7, HLA-DR11, HLA-DR13, HLA-DR15, HLA-DRB3, HLA-DRB4, HLA-DRB5 and HLA-DP4 molecules, preferably from the HLA-DR1, HLA-DR4, HLA-DR7, HLA-DR11, HLA-DR13, HLA-DR15, HLA-DRB5, HLA-DP401 and HLA-DP402 molecules.

Said HLA II molecules are advantageously encoded respectively by the HLA alleles DRB1*0101, DRB1*0301, DRB1*0401, DRB1*0701, DRB1*1101, DRB1*1301, DRB1*1501, DRB3*0101, DRB4*0101, DRB5*0101, DP*0401 and DP*0402.

Among these HLA II molecules predominant in the Caucasian population, the HLA-DP401 and HLA-DP402 molecules are also predominant in South America, in India, in Africa and in Japan.

Particularly advantageously, said peptide is capable of being presented by at least one HLA-DP401 or HLA-DP402 molecule.

According to another advantageous embodiment of said peptide, it is capable of being presented by at least three HLA II molecules predominant in the Caucasian population, preferably at least four HLA II molecules predominant in this population.

According to an advantageous arrangement of the above embodiments, said peptide is selected from the group consisting of the peptides of 15 amino acids located between the following positions of the alpha-isoform of survivin: 17 to 31, 19 to 33, 20 to 34, 84 to 98, 90 to 104, 91 to 105, 93 to 107, 96 to 110, 99 to 113, 122 to 136 and 128 to 142; these peptides have a good affinity (binding activity <1000 nM) for at least three HLA II molecules predominant in the Caucasian population.

Said peptide is advantageously selected from the group consisting of the sequences SEQ ID Nos: 5, 6, 7, 17, 19, 20, 21, 23, 24, 27 and 28.

Preferably, said peptide is selected from the group consisting of the peptides: 17-31, 19-33, 20-34, 84-98, 90-104, 91-105, 93-107, 96-110 and 128-142 which have a good affinity (binding activity <1000 nM) for at least four HLA II molecules predominant in the Caucasian population.

Notably, all the peptides which have a good affinity for at least four HLA II molecules predominant in the Caucasian population, with the exception of the peptide 128-142, also have a good affinity for at least one HLA-DP401 or HLA-DP402 molecule.

Such peptides make it possible both to obtain good vaccinal coverage in the individuals of the Caucasian population and to broaden the vaccinal coverage to individuals of other populations (South America, Africa, India and Japan).

Preferably, said peptide is selected from the group consisting of the peptides: 17-31, 19-33, 90-104, 93-107, 96-110 and 128-142.

Even more preferably, said peptide is selected from the group consisting of the peptides 19-33, 90-104 and 93-107.

According to another advantageous embodiment of said peptide, it has a sequence of 13, 14, 15, 16, 17, 18, 19, 20, 21, 22, 23, 24 or 25 amino acids.

According to another advantageous embodiment of said peptide, it is a variant of one of the above peptides, obtained by substitution of at least one of the residues P1, P6 and/or P9 for anchoring to the HLA II molecules, with an aromatic or hydrophobic amino acid, of the residue P6 with a cysteine (C), of the residue P9 with C, D, Q, S, T or E, and/or of the residue P4 with another natural or synthetic amino acid.

The term "natural or synthetic amino acid" is intended to mean the 20 natural α-amino acids commonly found in proteins (A, R, N, D, C, Q, E, G, H, I, L, K, M, F, P, S, T, W, Y and V), certain amino acids rarely encountered in proteins (hydroxyproline, hydroxylysine, methyllysine, dimethyllysine, etc.), the amino acids which do not exist in proteins, such as β-aniline, γ-aminobutyric acid, homocysteine, ornithine, citrulline, canavanine, norleucine, cyclohexylalanine, etc., and also the enantiomers and the diastereoisomers of the above amino acids.

The term "hydrophobic amino acid" is intended to mean an amino acid selected from (one-letter code): A, V, L, I, P, W, F and M.

The term "aromatic amino acid" is intended to mean an amino acid selected from (one-letter code): F, W and Y.

According to another advantageous embodiment of said peptide, it is labeled or complexed; it may in particular be complexed with labeled, for example biotinylated, HLA II molecules so as to form HLA II/peptide complexes, in particular multimeric complexes such as tetramers.

A subject of the present invention is also a polyepitopic fragment comprising the concatenation of at least two identical or different epitopes, at least one of which is a survivin CD4+ T epitope, included in a peptide as defined above, for use as an antigen in the prophylactic or therapeutic immunization against cancer or the diagnosis, prognosis or therapeutic monitoring of cancer.

Preferably, said polyepitopic fragment has a length of 20 to 1000 amino acids, preferably of 20 to 100 amino acids.

Said polyepitopic fragment advantageously comprises a tag fused to one of its ends, for the purification or the detection of said fragment. The tag, in particular a polyhistidine sequence or a B epitope of an antigen, is preferably separated from the polyepitopic sequence by a cleavage site for a protease so as to isolate the polyepitopic sequence from the fusion.

According to an advantageous embodiment of said polyepitopic fragment, it comprises the concatenation of at least one survivin CD4+ T epitope included in the peptide as defined above and of at least one epitope selected from the group consisting of:
 a survivin CD8+ T epitope presented by an HLA 1 molecule and recognized by cytotoxic T lymphocytes specific for said antigen; such CD8+ T epitopes are in particular described on the site preferably, the CD8+ T epitope is chosen from: survivin 96-104 (LTLGEFLKL, SEQ ID No. 37) or 95-104 (LTLGEFLKL, SEQ ID No. 38), survivin-2B 80-88 (AYACNTSTL, SEQ ID No. 39) and the peptides as described in table I of Bachinsky et al., Cancer Immun., 2005, 5, 6;
 a natural or synthetic, universal CD4+ T epitope such as the tetanus toxin peptide TT 830-846 (O'Sullivan et al., J. Immunol., 1991, 147, 2663-2669), the flu virus hemaglutinin peptide HA 307-319 (O'Sullivan et al., mentioned above), the PADRE peptide (KXVAAWTLKAA, SEQ ID No. 41; Alexander et al., Immunity, 1994, 1, 751-761) and peptides derived from the *Plasmodium falciparum* antigens, such as the CS.T3 peptide (Sinigaglia et al., Nature, 1988, 336, 778-780) and the CSP, SSP2, LSA-1 and EXP-1 peptides (Doolan et al., J. Immunol., 2000, 165, 1123-1137);
 a B epitope formed by a sugar (Alexander et al., mentioned above), said B epitope preferably being in the form of a glycopeptide; and
 a survivin B epitope recognized specifically by antibodies directed against said tumor antigen.

The combination of the CD4+ T epitope with at least one of the epitopes as defined above advantageously makes it possible to trigger or to modulate an antitumor immune response.

A subject of the present invention is also a lipopeptide comprising a peptide or a polyepitopic fragment as defined above, for use as an antigen in the prophylactic or therapeutic immunization against cancer or the diagnosis, prognosis or therapeutic monitoring of cancer.

Said lipopeptide is in particular obtained by addition of a lipid to an α-amino function or to a reactive function of the side chain of an amino acid of said peptide or polyepitopic fragment; it may comprise one or more chains derived from $C_4$-$C_{20}$ fatty acids, optionally branched or unsaturated (palmitic acid, oleic acid, linoleic acid, linolenic acid, 2-amino-hexadecanoic acid, pimelautide, trimexautide) or a derivative of a steroid. The preferred lipid portion is in particular represented by an $N^\alpha$-acetyllysine $N^\epsilon$ (palmitoyl) group, also called Ac-K (Pam).

A subject of the present invention is also a fusion protein consisting of a protein or a protein fragment, fused with a peptide or a polyepitopic fragment as defined above, for use as an antigen in the prophylactic or therapeutic immunization against cancer or the diagnosis, prognosis or therapeutic monitoring of cancer.

The peptide or the polyepitopic fragment may be fused with the $NH_2$— or COOH— end of said protein, or inserted into the sequence of said protein.

According to an advantageous embodiment of said fusion protein, it consists of a peptide as defined above, fused with a sequence for targeting to the endosome, preferably derived from a human invariable chain Ii or from the LAMP-1 protein. The sequences for targeting to the endosome and their use for targeting antigens to the endosome are in particular described in Sanderson et al. (P.N.A.S., 1995, 92, 7217-7222), Wu et al. (P.N.A.S., 1995, 92, 11671-11675) and Thompson et al. (J. Virol., 1998, 72, 2246-2252).

According to another advantageous embodiment of said fusion protein, it consists of a peptide as defined above, fused with one of the chains of an HLA II molecule, preferably the beta-chain, or else with a fragment thereof corresponding to a soluble HLA II molecule, in particular a fragment corresponding to the extracellular domain preceded by the homologous signal peptide or by a heterologous signal peptide. Said peptide is advantageously inserted between the signal peptide and the $NH_2$-end of the extracellular domain of the β-chain, as described for the HLA-DR molecule (Kolzin et al., PNAS, 2000, 97, 291-296).

Alternatively, said peptide or said polyepitopic fragment is fused with a protein, known to those skilled in the art, for facilitating its purification or its detection, such as in particular glutathione-S-transferase (GST) and fluorescent proteins (GFP and derivatives). In this case, the sequence of the peptide or of the polyepitopic fragment of interest is preferably separated from the rest of the protein by a cleavage site for a protease, in order to facilitate the purification of said peptide or of said polyepitopic fragment.

A subject of the present invention is also an expression vector comprising a polynucleotide encoding a peptide, a polyepitopic fragment or a fusion protein as defined above, under the control of appropriate regulatory sequences for transcription and, optionally, for translation, for use as an antigen in the prophylactic or therapeutic immunization against cancer or the diagnosis or prognosis of cancer.

In accordance with the invention, the sequence of said polynucleotide is that of the cDNA encoding said peptide or polyepitopic fragment or said fusion protein. Said sequence may advantageously be modified in such a way that the codon usage is optimal in the host in which it is expressed. In addition, said polynucleotide may be linked to at least one heterologous sequence.

For the purpose of the present invention, the expression "heterologous sequence relative to a nucleic acid sequence encoding survivin" is intended to mean any nucleic acid sequence other than those which, naturally, are immediately adjacent to said nucleic acid sequence encoding said survivin peptide.

In accordance with the invention, said recombinant vector comprises an expression cassette including at least one polynucleotide as defined above, under the control of appropriate regulatory sequences for transcription and, optionally, for translation (promoter, enhancer, intron, initiation codon (ATG), stop codon, polyadenylation signal).

Numerous vectors into which it is possible to insert a nucleic acid molecule of interest in order to introduce it into and to maintain it in a eukaryotic or prokaryotic host cell are known in themselves; the choice of an appropriate vector depends on the use envisioned for this vector (for example, replication of the sequence of interest, expression of this sequence, maintenance of this sequence in extrachromosomal form, or else integration into the chromosomal material of the host), and also on the nature of the host cell. For example, use may be made, inter alia, of viral vectors such as adenoviruses, retroviruses, lentiviruses, AAVs and baculoviruses, into which the sequence of interest has been inserted beforehand; said sequence (isolated or inserted into a plasmid vector) may also be combined with a substance which allows it to cross the membrane of the host cells, for instance a transporter such as a nanotransporter or a preparation of liposomes or of cationic polymers, or else it may be introduced into said host cell using physical methods such as electroporation or microinjection. In addition, these methods may advantageously be combined, for example using electroporation combined with liposomes.

A subject of the present invention is also an immunogenic or vaccinal composition, characterized in that it comprises at least one peptide, one polyepitopic fragment, one fusion protein, one lipopeptide or one vector as defined above, and a pharmaceutically carrier, a carrier substance or an adjuvant.

The immunogenic composition according to the invention is in a pharmaceutical form suitable for parenteral (subcutaneous, intramuscular, intravenous), enteral (oral, sublingual) or local (rectal, vaginal) administration.

The pharmaceutically acceptable carriers, the carrier substances and the adjuvants are those conventionally used.

The adjuvants are advantageously chosen from the group consisting of: oily emulsions, mineral substances, bacterial extracts, saponin, alumina hydroxide, monophosphoryl-lipid A and squalene.

The carrier substances are advantageously selected from the group consisting of: unilamellar or multilamellar liposomes, ISCOMs, virosomes, viral pseudoparticles, saponin micelles, solid microspheres which are saccharide (poly (lactide-co-glycolide)) or gold-bearing in nature, and nanoparticles.

According to an advantageous embodiment of said composition, it comprises at least one survivin CD4+ T epitope and one survivin CD8+ T epitope in the form of a mixture of peptides, of a polyepitopic fragment and/or of an expression vector encoding said peptides or said fragment, as defined above.

According to an advantageous arrangement of this embodiment of said composition, the CD8+ T epitope is chosen from: survivin 96-104 (LTLGEFLKL) or 95-104 (LTLGEFLKL), survivin-2B 80-88 (AYACNTSTL) and the peptides as described in table I of Bachinsky et al., Cancer Immun., 2005, 5, 6.

According to another advantageous embodiment of said composition, it comprises at least two survivin peptides including a CD4+ T epitope as defined above, selected from the group consisting of one of the following combinations:
  peptide 17-31 and at least one of peptides 19-33, 90-104 or 128-142,
  peptide 19-33 and peptide 96-110,
  peptide 90-104 and peptide 17-31,
  peptide 96-110 and peptide 90-104, and
  peptides 93-107 and 128-142, and at least one of peptides 17-31, 19-33, 96-110 or 90-104.

Such combinations make it possible to advantageously induce CD4+ T lymphocytes in virtually all individuals immunized.

According to yet another advantageous embodiment of said composition, it comprises a peptide including a universal CD4+ T epitope, as defined above.

A subject of the present invention is also the use of at least one peptide, one polyepitopic fragment, one fusion protein, one lipopeptide and/or one vector as defined above, for the preparation of a vaccine for use in the prevention or treatment of cancer.

The peptides according to the present invention and the derived products (polyepitopic fragment, fusion protein, lipopeptide, recombinant vector) may be used in immunotherapy in the treatment of tumors overexpressing survivin. Said peptides or derived products are used either as a vaccine or in cell therapy, or else through a combination of the two approaches.

Cell therapy comprises the preparation of antigen-presenting cells (dendritic cells) by a conventional protocol comprising the isolation of peripheral blood mononuclear cells (PBMCs) from a patient to be treated and the culturing of the dendritic cells in the presence of peptide(s). In a second step, the antigen-presenting cells loaded with the peptide are reinjected into the patient.

A subject of the present invention is also the use of at least one peptide, one polyepitopic fragment, one fusion protein, one lipopeptide and/or one vector as defined above, for the preparation of a reagent for diagnosing, evaluating the prognosis or monitoring the treatment of a cancer. Preferably, said reagent comprises a peptide or a fusion protein as defined above, optionally labeled or complexed, in particular complexed with labeled, for example biotinylated, HLA II molecules, in the form of multimeric complexes such as tetramers.

A subject of the present invention is also an in vitro method for diagnosing, evaluating the prognosis or monitoring the treatment of a cancer in an individual, characterized in that it comprises:
  bringing a biological sample from said individual into contact with a peptide as defined above, and
  detecting survivin-specific CD4+ T lymphocytes by any appropriate means.

A subject of the present invention is also a kit for diagnosing, evaluating the prognosis or monitoring the treatment of a cancer, characterized in that it comprises at least one peptide as defined above and, optionally, a reagent for detecting CD4+ T lymphocytes.

The method according to the invention makes it possible to monitor the evolution of the CD4+ T response directed against survivin over the course of a cancer or else of an antitumor treatment, in particular an antitumor immunotherapy; the survivin-specific CD4+ T lymphocytes may be of TH1 type (secretion of IFN-γ), TH2 type (secretion of IL-4) or regulatory T type (secretion of IL-10 or of TGF-β); it is expected that the TH1-type T response is the sign of a favorable evolution of the cancer, whereas the regulatory T response is the sign of an unfavorable evolution of this cancer. The detection is carried out using a biological sample containing CD4+ T cells, in particular a sample of mononuclear cells isolated from a peripheral blood sample (PBMCs).

The survivin-specific CD4+ T lymphocytes are detected by any means, known in themselves. For example, use may be made of direct means such as flow cytometry in the presence of multimeric complexes as defined above, or else indirect means such as lymphocyte proliferation assays and assays for cytokines such as IL-2, IL-4, IL-5, IL-10 and IFN-γ, in particular by immunoenzymatic techniques (ELISA, RIA, ELISPOT) or by flow cytometry (assaying of intracellular cytokines).

More specifically:

A suspension of cells (PBMCs, PBMCs depleted of CD8+ cells, T lymphocytes pre-enriched by means of an in vitro culture step with the peptides as defined above or cloned T lymphocytes) is cultured for 3 to 5 days in the presence of said peptides and, as required, of appropriate presenting cells, such as dendritic cells, autologous or heterologous PBMCs, lymphoblastoid cells such as those obtained after infection with the EBV virus, or genetically modified cells. The presence of survivin-specific CD4+ T cells in the initial suspension is detected by means of the peptides, according to one of the following methods:

Proliferation Assay:

The proliferation of the survivin-specific CD4+ T cells is measured by incorporation of tritiated thymidine into the DNA of the cells.

ELISPOT Assay:

The ELISPOT assay makes it possible to reveal the presence of T cells secreting cytokines (IL-2, IL-4, IL-5, IL-10 and IFN-γ), specific for a peptide as defined above. The principle of this assay is described in Czerkinsky et al., J. Immunol. Methods, 1983, 65, 109-121 and Schmittel et al., J. Immunol. Methods, 1997, 210, 167-174, and its implementation is illustrated in international application WO 99/51630 or Gahéry-Ségard et al., J. Virol., 2000, 74, 1694-1703.

Detection of Cytokines:

The presence of survivin-specific T cells secreting cytokines such as IL-2, IL-4, IL-5, IL-10 and IFN-γ is detected either by assaying the cytokines present in the culture supernatant, by means of an immunoenzymatic assay, in particular using a commercial kit, or by detecting the intracellular cytokines by flow cytometry. The principle of detection of the intracellular cytokines is described in Goulder et al., J. Exp. Med., 2000, 192, 1819-1832 and Maecker et al., J. Immunol. Methods, 2001, 255, 27-40 and its implementation is illustrated in Draenert et al., J. Immunol. Methods, 2003, 275, 19-29.

Multimeric Complexes a biological sample, preferably peripheral blood mononuclear cells (PBMCs), is brought into contact with labeled multimeric complexes, in particular labeled with a fluorochrome, formed by binding between soluble HLA II molecules and peptides as defined above, and the cells labeled with said multimeric complexes are analyzed, in particular by flow cytometry.

Advantageously, prior to the biological sample being brought into contact with said complexes, it is enriched in CD4+ T cells by bringing it into contact with anti-CD4 antibodies.

The HLA II/peptide multimeric complexes can be prepared from natural molecules extracted from cells expressing an HLA II molecule or from recombinant molecules produced in appropriate host cells as specified, for example, in Novak et al. (J. Clin. Investig., 1999, 104, R63-R67) or in Kuroda et al. (J. Virol., 2000, 74, 18, 8751-8756). These HLA II molecules may in particular be truncated (deletion of the transmembrane domain) and their sequence may be modified in order to make them soluble or else to facilitate the pairing of the alpha- and beta-chains (Novak et al., mentioned above).

The loading of HLA II molecules with the peptide may be carried out by bringing a preparation of HLA II molecules as above into contact with the peptide. For example, biotinylated, soluble HLA II molecules are incubated, for 72 hours at 37° C., with a 10-fold excess as defined above, in a 10 mM phosphate-citrate buffer containing 0.15 M NaCl, at a pH of between 4.5 and 7.

Alternatively, the sequence of the peptide may be introduced into one of the chains of the HLA II molecule in the form of a fusion protein which allows the preparation of HLA II/peptide multimeric complexes from appropriate host cells expressing said fusion protein. Said complexes may then be labeled, in particular with biotin.

The multimeric complexes of tetramer type are in particular obtained by adding, to the loaded HLA II molecules, streptavidin labeled with a fluorochrome in an amount four times less (mole for mole) with respect to the HLA II molecules, the whole mixture then being incubated for a sufficient period of time, for example overnight at ambient temperature.

The multimeric complexes may also be formed either by incubation of HLA II/peptide monomers with magnetic beads coupled to streptavidin, as described for HLA I molecules (Bodinier et al., Nature, 2000, 6, 707-710), or by insertion of HLA II/peptide monomers into lipid vesicles as described for murine MHC class II molecules (Prakken, Nature Medicine, 2000, 6, 1406-1410).

To use these HLA II/peptide multimeric complexes, in particular of tetramer type, a suspension of cells (PBMCs, PBMCs depleted of CD8+ cells, T lymphocytes pre-enriched by means of an in vitro culture step with peptides as defined above, or cloned T lymphocytes) is brought into contact with HLA II/peptide multimeric complexes at an appropriate concentration (for example of the order of 10 to 20 μg/ml), for a period of time sufficient to allow binding between the complexes and the survivin-specific CD4+ T lymphocytes (for example, of the order of 1 to 3 hours). After washing, the suspension is analyzed by flow cytometry: the labeling of the cells is visualized by means of the multimeric complexes which are fluorescent.

The flow cytometry makes it possible to separate the cells labeled with the HLA II/peptide multimeric complexes from the unlabeled cells and thus to perform cell sorting.

A subject of the present invention is thus also a method for sorting survivin-specific CD4+ T lymphocytes, characterized in that it comprises at least the following steps:

bringing a cell sample into contact, in vitro, with labeled HLA II/peptide multimeric complexes, in particular labeled with a fluorochrome, said complexes being formed by binding of soluble HLA II molecules with at least one peptide as defined above, and sorting the cells bound to said HLA II/peptide complexes, in particular by flow cytometry.

A subject of the present invention is also a peptide as defined above, with the exclusion of the peptide located between positions 89 and 101 of the alpha-isoform of survivin (peptide 89-101).

A subject of the present invention is also a polyepitopic fragment, a fusion protein, a lipopeptide, a polynucleotide, an expression cassette, a recombinant vector and a modified prokaryotic or eukaryotic host cell, as defined above.

The invention encompasses in particular:
a) expression cassettes comprising at least one polynucleotide as defined above, under the control of appropriate regulatory sequences for transcription and, optionally, for translation (promoter, enhancer, intron, initiation codon (ATG), stop codon, polyadenylation signal), and
b) recombinant vectors comprising a polynucleotide in accordance with the invention. Advantageously, these vectors are expression vectors comprising at least one expression cassette as defined above.

The polynucleotides, the recombinant vectors and the transformed cells as defined above can be used in particular for the production of the peptides, polyepitopic fragments and fusion proteins according to the invention.

The polynucleotides according to the invention are obtained by the conventional methods, known in themselves, according to standard protocols such as those described in *Current Protocols in Molecular Biology* (Frederick M. AUSUBEL, 2000, Wiley and son Inc, Library of Congress, USA). For example, they may be obtained by amplification of a nucleic sequence by PCR or RT-PCR, by screening genomic DNA libraries by hybridization with a homologous probe, or else by complete or partial chemical synthesis. The recombinant vectors are constructed and introduced into host cells by conventional recombinant DNA and genetic engineering methods, which are known in themselves.

The peptides and their derivatives (variants, modified peptides, lipopeptides, polyepitopic fragments, fusion proteins) as defined above are prepared by conventional techniques known to those skilled in the art, in particular by solid-phase or liquid-phase synthesis or by expression of a recombinant DNA in an appropriate cell system (eukaryotic or prokaryotic).

More specifically:
the peptides and their derivatives (variants, polyepitopic fragments) may be solid-phase synthesized according to the Fmoc technique, originally described by Merrifield et al. (J. Am. Chem. Soc., 1964, 85: 2149-), and purified by reverse-phase high performance liquid chromatography;
the lipopeptides may in particular be prepared according to the method described in international applications WO 99/40113 or WO 99/51630;
the peptides and derivatives such as the variants, the polyepitopic fragments and the fusion proteins may also be produced from the corresponding cDNAs, obtained by any means known to those skilled in the art; the cDNA is cloned into a eukaryotic or prokaryotic expression vector and the protein or the fragment produced in the cells modified with the recombinant vector is purified by any appropriate means, in particular by affinity chromatography.

Example 1: Binding Activity of the Survivin Peptides with Respect to HLA II Molecules 1) Materials and Methods
a) Peptides and Proteins Peptides of 15 amino acids (15-mers) covering the entire survivin sequence (SwissProt O15392) were selected according to the presence of aromatic or hydrophobic residues at position 1 to 5, in particular at position 3 or 4, for anchoring in pocket P1 of the HLA-DR and HLA-DP4 molecules.

The sequences of the selected peptides are given in table II and the sequence listing attached in the annex.

The peptides were synthesized according to the Fmoc strategy by solid-phase parallel synthesis (357 MPS synthesizer, Advanced Chemtech Europe), optionally purified by RP-HPLC (Vydac $C_{18}$ column, Interchim) and controlled by mass spectrometry (ES-MS) and analytical HPLC.

The survivin (Bir5 or BIR5) and the HIV Nef protein are produced in *E. coli*, in the form of fusion proteins with glutathione-S-transferase (GST), purified on a glutathione column and separated from the GST by proteolytic cleavage.

TABLE II

Sequences of the survivin peptides (SEQ ID Nos. 1 to 28)

| SEQ ID No. | Positions | sequence |
|---|---|---|
| 1 | 1-15* | M G A P T L P P A W Q P F L K |
| 2 | 4-18 | P T L P P A W Q P F L K D H R |
| 3 | 8-22 | P A W Q P F L K D H R I S T F |
| 4 | 11-25 | Q P F L K D H R I S T F K N W |
| 5 | 17-31 | H R I S T F K N W P F L E G C |
| 6 | 19-33 | I S T F K N W P F L E G C A C |
| 7 | 20-34 | S T F K N W P F L E G C A C T |
| 8 | 23-37 | K N W P F L E G C A C T P E R |
| 9 | 36-50 | E R M A E A G F I H C P T E N |
| 10 | 41-55 | A G F I H C P T E N E P D L A |

TABLE II-continued

Sequences of the survivin peptides (SEQ ID Nos. 1 to 28)

| SEQ ID No. | Positions | sequence |
|---|---|---|
| 11 | 52-66 | P D L A Q C F F C F K E L E G |
| 12 | 56-70 | Q C F F C F K E L E G W E P D |
| 13 | 59-73 | F C F K E L E G W E P D D D P |
| 14 | 62-76 | K E L E G W E P D D D P I E E |
| 15 | 65-79 | E G W E P D D D P I E E H K K |
| 16 | 72-86 | D P I E E H K K H S S G C A F |
| 17 | 84-98 | C A F L S V K K Q F E E L T L |
| 18 | 87-101 | L S V K K Q F E E L T L G E F |
| 19 | 90-104 | K K Q F E E L T L G E F L K L |
| 20 | 91-105 | K Q F E E L T L G E F L K L D |
| 21 | 93-107 | F E E L T L G E F L K L D R E |
| 22 | 94-108 | E E L T L G E F L K L D R E R |
| 23 | 96-110 | L T L G E F L K L D R E R A K |
| 24 | 99-113 | G E F L K L D R E R A K N K I |
| 25 | 102-116 | L K L D R E R A K N K I A K E |
| 26 | 111-125 | N K I A K E T N N K K K E F E |
| 27 | 122-136 | K E F E E T A K K V R R A I E |
| 28 | 128-142 | A K K V R R A I E Q L A A M D |

*the positions are numbered with reference to the sequence of human survivin of 142 amino acids (SwissProt 015392).

b) HLA II/Peptide Binding Assay

The assays for binding to HLA II molecules are competitive binding assays with immunoenzymatic visualization, as described in U.S. Pat. No. 6,649,166, Texier et al., J. Immunol., 2000, 164, 3177-3184 and Texier et al., Eur. J. Immunol., 2001, 31, 1837-1846, for the HLA-DR molecules, and in PCT international application WO 03/040299 and Castelli et al., J. Immunol., 2002, 169, 6928-6934, for the HLA-DP4 molecule. The use of these assays for measuring the binding activity of peptides derived from various antigens is illustrated in U.S. Pat. No. 6,649,166 and PCT international applications WO 02/090382, WO 03/040299 and WO 2004/014936.

More specifically, the peptides: HA 306-318 (PKYVKQNTLKLAT, SEQ ID No. 29), A3 152-166 (EAEQLRAYLDGTGVE, SEQ ID No. 30), MT 2-16 (AKTIAYDEEARRGLE, SEQ ID No. 31), B1 21-36 (TERVRLVTRHIYNREE, SEQ ID No. 32), YKL (AAYAAAKAAALAA, SEQ ID No. 33), LOL 191-210 (ESWGAVWRIDTPDKLTGPFT, SEQ ID No. 34), E2/E168 (AGDLLAIETDKATI, SEQ ID No. 35) and Oxy 271-287 (EKKYFAATQFEPLAARL, SEQ ID No. 36), biotinylated at the $NH_2$-terminal residue, according to the protocol described in Texier et al., J. Immunol., 2000, 164, 3177-3184, are used as tracer under the conditions as specified in the table below.

TABLE III

Conditions for the assays for binding to HLA II molecules

| Alleles | HLA II dilution | Tracers | Tracer concentration (nM) | Optimal pH | Incubation time (h) | $IC_{50}$ (nM) |
|---|---|---|---|---|---|---|
| DRB1*0101 | 1/200 | HA 306-318 | 1 | 6 | 24 | 5.5 |
| DRB1*0301 | 1/40 | MT 2-16 | 200 | 4.5 | 72 | 450 |
| DRB1*0401 | 1/80 | HA 306-318 | 30 | 6 | 24 | 50 |
| DRB1*0701 | 1/60 | YKL | 10 | 5 | 24 | 15 |
| DRB1*1101 | 1/80 | HA 306-318 | 10 | 5 | 24 | 25 |
| DRB1*1301 | 1/40 | B1 21-36 | 100 | 4.5 | 72 | 800 |
| DRB1*1501 | 1/100 | A3 152-166 | 30 | 4.5 | 72 | 52 |
| DRB5*0101 | 1/80 | HA 306-318 | 10 | 5.5 | 24 | 8 |
| DRB3*0101 | 1/40 | Lol 191-120 | 10 | 5.5 | 24 | 14 |
| DRB4*0101 | 1/20 | E2/E168 | 10 | 5 | 72 | 15 |
| DRB1*0401 | 1/80 | Oxy 271-287 | 1 | 5 | 24 | 10 |
| DRB1*0402 | 1/40 | Oxy 271-287 | 1 | 5 | 24 | 6.5 |

The results are expressed in the form of the concentration (nM) of competitive peptide which inhibits 50% of the maximum binding of the biotinylated tracer peptide ($IC_{50}$). The sensitivity of each assay is reflected by the $IC_{50}$ values observed with the nonbiotinylated peptides which correspond to the tracers; the $IC_{50}$ values of the tracers vary by a factor of less than three. A peptide having a binding activity ($IC_{50}$) with respect to an HLA II molecule of less than 1000 nM has a good affinity for this HLA II molecule, a peptide having a binding activity ($IC_{50}$) with respect to an HLA II molecule of less than 100 nM has a strong affinity for this HLA II molecule.

2) Results

Three distinct regions of survivin are capable of binding with a good affinity ($IC_{50}$<1000 nM) to at least three predominant HLA II molecules, in particular predominant in the Caucasian population: regions 17-34 (N-terminal), 84-113 and 122-142 (C-terminal) (table IV).

TABLE IV

Binding activities of the survivin peptides with respect to the 12 predominant HLA II molecules° ($IC_{50}$ in nM)

| Peptides | DR1 | DR3 | DR4 | DR7 | DR11 | DR13 | DR15 |
|---|---|---|---|---|---|---|---|
| Ref.** | 2 | 346 | 33 | 16 | 10 | 609 | 41 |
| 1-15 | 10800 | >100000 | >100000 | >100000 | 63 | >100000 | 80000 |
| 4-18 | 45000 | >100000 | >100000 | >100000 | 33 | 40000 | >100000 |
| 8-22 | 6573 | 16000 | 46000 | 9391 | 41 | 2314 | 5200 |
| 11-25 | 6000 | 65000 | 45000 | 8000 | 329 | 2408 | 22 |
| 17-31 | 19 | >100000 | 9200 | 18 | 247 | 735 | 3 |
| 19-33 | 10 | >100000 | 615 | 748 | 147 | 9500 | 81 |
| 20-34 | 11 | >100000 | 5200 | 20000 | 210 | 2449 | 1304 |
| 23-37 | 71 | >100000 | 5200 | 60000 | 37000 | >100000 | >100000 |
| 36-50 | 2550 | >100000 | 17000 | 17000 | 5586 | >100000 | >100000 |
| 41-55 | 2315 | >100000 | 5000 | 3735 | 1148 | >100000 | 7000 |
| 52-66 | 4100 | 11832 | 22000 | 6673 | 92 | 23000 | 2245 |
| 56-70 | 1597 | >100000 | >100000 | 13000 | 363 | >100000 | 3000 |
| 59-73 | 3759 | >100000 | 58000 | 9000 | 1844 | >100000 | 8000 |
| 62-76 | >100000 | >100000 | >100000 | >100000 | >100000 | >100000 | 65000 |
| 65-79 | >100000 | >100000 | >100000 | >100000 | >100000 | >100000 | >100000 |
| 72-86 | 95000 | >100000 | >100000 | >100000 | >100000 | 11000 | >100000 |
| 84-98 | 2828 | 2569 | 19000 | 179 | 10 | 845 | 574 |
| 87-101 | 150 | >100000 | 6450 | 705 | 2062 | >100000 | 4796 |
| 90-104 | 40 | >100000 | 748 | 140 | 2349 | >100000 | 7500 |
| 91-105 | 12 | >100000 | 1587 | 56 | 2353 | >100000 | 3162 |
| 93-107 | 128 | >100000 | 5500 | 2793 | 548 | 7800 | 612 |
| 94-108 | n.d*. | n.d. | n.d. | n.d. | n.d. | n.d. | n.d. |
| 96-110 | 18 | 5477 | 1666 | 5639 | 7 | 302 | 490 |
| 99-113 | 48 | 4673 | 2134 | 6462 | 40 | 9165 | 1200 |
| 102-116 | 7746 | >100000 | >100000 | 50000 | 8944 | >100000 | >100000 |
| 111-125 | 5000 | >100000 | >100000 | >100000 | 30000 | 70000 | 90000 |
| 122-136 | 5557 | 5809 | >100000 | 20000 | 310 | 995 | 1200 |
| 128-142 | 8 | 12000 | 352 | 1342 | 25 | >100000 | 284 |

| Peptides | DRB3 | DRB4 | DRB5 | DP401 | DP402 | No. of molecules |
|---|---|---|---|---|---|---|
| Ref.** | 16 | 24 | 8 | 15 | 25 | fixed |
| 1-15 | >100000 | >100000 | 8000 | 9200 | 6928 | 1 |
| 4-18 | >100000 | >100000 | 5477 | 8998 | 3594 | 1 |
| 8-22 | 8718 | 29000 | 2191 | 21000 | 10450 | 1 |
| 11-25 | 3674 | 75000 | 2258 | 33000 | 25000 | 2 |
| 17-31 | >100000 | 7500 | 302 | 40 | 29 | 8 |
| 19-33 | >100000 | 3118 | 3779 | 32 | 24 | 7 |
| 20-34 | >100000 | 5500 | 6500 | 210 | 114 | 4 |
| 23-37 | >100000 | >100000 | 3421 | >100000 | 3700 | 1 |
| 36-50 | >100000 | 49000 | 3795 | 3622 | 3169 | 0 |
| 41-55 | 10000 | 328 | 3382 | >100000 | >100000 | 1 |
| 52-66 | 12649 | >100000 | 5348 | >100000 | 4583 | 1 |
| 56-70 | 12000 | >100000 | 20000 | >100000 | >100000 | 1 |
| 59-73 | >100000 | >100000 | 45000 | >100000 | >100000 | 0 |
| 62-76 | 29000 | >100000 | >100000 | >100000 | >100000 | 0 |
| 65-79 | >100000 | >100000 | >100000 | >100000 | >100000 | 0 |
| 72-86 | >100000 | >100000 | 6200 | >100000 | >100000 | 0 |
| 84-98 | 11832 | 1327 | 1766 | 167 | 113 | 5 |
| 87-101 | 6797 | 9798 | 6000 | 3666 | 6387 | 2 |
| 90-104 | 48000 | >100000 | 280 | 48 | 19 | 6 |
| 91-105 | 30000 | >100000 | 145 | 11 | 12 | 5 |
| 93-107 | 45000 | >100000 | 529 | 20 | 67 | 6 |
| 94-108 | n.d. | n.d. | n.d. | n.d. | n.d. | 0 |
| 96-110 | >100000 | 3600 | 103 | 2915 | 620 | 6 |
| 99-113 | >100000 | 22000 | 22 | 40000 | >100000 | 3 |
| 102-116 | >100000 | >100000 | 18 | >100000 | >100000 | 1 |
| 111-125 | >100000 | 70000 | 16 | >100000 | >100000 | 1 |
| 122-136 | >100000 | >100000 | 447 | >100000 | >100000 | 3 |
| 128-142 | >100000 | 1803 | 1090 | 13000 | 20000 | 4 |

°the values are the results of 3 independent experiments; they do not vary by more than a factor of 3 between the experiments.
*not determined (insoluble peptide)
**tracer binding activity On the other hand, the peptides derived from the rest of the sequence do not exhibit any significant binding activity for at least three HLA II molecules predominant in the Caucasian population. In addition, no peptide binds to the DR3 and DRB3 molecules.

Certain peptides are specific for an allele, such as the peptides 1-15, 4-18 and 52-66 which bind only to the HLA-DR11 molecule, and the peptide 41-55 which binds only to the HLA-DRB4 molecule.

The peptides of the N-terminal region have a good affinity for the HLA-DR1, DR7, DR11, DR13, DR15, DRB5, DP401 and DP402 molecules.

In region 84-113, the binding capacities of the four overlapping peptides 84-98, 90-104, 93-107 and 96-110 cover the HLA-DR1, DR4, DR7, DR11, DR13, DR15, DRB5, DP401 and DP402 molecules. Peptide 91-105 has a high affinity for the DR1, DR7, DRB5, DP401 and DP402 molecules.

In the C-terminal region, peptide 128-142 binds with a high affinity to the DR1 and DR11 molecules and a lower affinity to the HLA-DR4 and HLA-DR15 molecules.

Seven peptides which have a good affinity for at least four HLA II molecules predominant in the Caucasian population, chosen from HLA-DR1, -DR4, -DR7, -DR11, -DR15, DRB5, DP401 and DP402, were chosen for the immunogenicity tests: 17-31, 20-34, 84-98, 90-104, 93-107, 96-110 and 128-142.

Example 2: Immunogenicity of the Survivin Peptides In Vitro

The ability of the peptides having a good affinity for the HLA II molecules predominant in the Caucasian population, to induce a stimulation of specific T lymphocytes, in vitro, was evaluated using blood samples from normal individuals (not carrying a tumor). The aim is to evaluate the ability to recruit CD4+ precursor lymphocytes, although, in a naïve individual, they are at a very low frequency, i.e. to perform an in vitro immunization by means of these peptides.

1) Materials and Methods
a) Individuals Tested

The peripheral blood mononuclear cells (PBMCs) of seven normal donors were separated on a Ficoll gradient (Ficoll-Hypaque, Sigma-Aldrich) and then the HLA-DR and HLA-DP genotype of the donors was determined by SSP, using the Olerup SSP™ HLA-DPB1 and HLA-DRB1 kit (Olerup SSP AB). The HLA-DRB1 and HLA-DPB1 alleles of these individuals are given in table V.

TABLE V

| HLA typing of the individuals tested | | | | |
|---|---|---|---|---|
| Normal donor | DRB1 | | Second DR molecule | DPB1 |
| D169 | DRB1*1502 | | | DPB1*0402 |
| D171 | DRB1*0101 | DRB1*0401 | DRB4 | DPB1*0401 |
| D174 | DRB1*0701 | DRB1*1501 | DRB4 | DRB5 DPB1*0401 |
| D179 | DRB1*0701 | DRB1*1301 | DRB4 | DRB3 |
| D187 | DRB1*0701 | DRB1*0401 | DRB4 | |
| D188 | DRB1*1101 | | DRB3 | DPB1*0401 |
| D180 | DRB1*0101 | DRB1*1101 | | DPB1*0401 | b) Production of CD4+ T Lymphocyte Lines Specific for Survivin and Restricted to the Predominant HLA II Molecules Peripheral blood mononuclear cells (PBMCs) were separated on a Ficoll gradient (Ficoll-Hypaque, Sigma-Aldrich). The PBMCs were then cultured in AIM V medium (Life Technologies; $10^7$ cells/ml) and incubated in flasks, in an incubator at 37° C. in the presence of a 5% $CO_2$. After incubation overnight, the nonadherent cells were recovered and the CD4+ T lymphocytes were then purified using anti-CD4 antibodies coupled to magnetic beads (Myltenyi Biotech kit), sorted by flow cytometry (MACS) according to the manufacturer's recommendations (Myltenyi Biotech), and frozen. The adherent cells were incubated for 5 to 6 days, in AIM V medium containing 1000 U/ml of recombinant human GM-CSF and 1000 U/ml of recombinant human IL-4 (rh-GM-CSF and rh-IL-4; Tebu), and the cells that had differentiated into dendritic cells (immature dendritic cells) were subsequently cultured for 2 days in the presence of 1 µg/ml of LPS (Sigma), 1000 U/ml of rh-IL-4 and 1000 U/ml of rh-GM-CSF, so as to induce their maturation.

The quality of the dendritic cell preparations is evaluated by flow cytometry (FACScalibur Flow Cytometer™, Becton Dickinson) assisted by the Cell Quest Pro™ software (Becton Dickinson). To do this, the dendritic cells are labeled with anti-CD14, -CD86, -HLA-DR, -CD80 (Becton Dickinson), -Cd1a, -HLA-ABC, -CD83 and -CD16 (Beckman Coulter) antibodies, conjugated to a fluorochrome.

The mature dendritic cells (DCs; $5 \times 10^5$ cells in 1 ml) thus obtained were incubated with a mixture of peptides (10 µg of each peptide) in IMDM medium (Invitrogen) supplemented with glutamine (24 mM, Sigma), asparagines (55 mM, Sigma), arginine (150 mM, Sigma), penicillin (50 IU/ml, Invitrogen), streptomycin (50 mg/ml, Invitrogen) and 10% of human serum, hereinafter referred to as complete IMDM medium, for 4 hours at 37° C. The mature dendritic cells were subsequently washed and then incubated, in the presence of previously thawed autologous CD4+ T lymphocytes ($10^4$ DCs and $10^5$ CD4+ T), in 200 µl of complete IMDM medium containing 1000 U/ml of IL-6 (R&D systems) and 10 ng/ml of IL-12 (R&D systems). After 7 days (D7), the culture was stimulated a first time, by means of mature dendritic cells previously thawed and loaded with the mixture of peptides, in the medium containing IL-2 (10 U/ml) and IL-7 (5 ng/ml). After a further two stimulations (D14 and D21) by means of loaded dendritic cells, under the same conditions, the specificity of the cells for the peptides was analyzed at D28 and D29, by measuring the production of IFN-γ by ELISPOT.

c) Production of HLA-DP4-Restricted Survivin-Specific CD4+ T Lymphocyte Lines

HLA-DP4-restricted survivin-specific CD4+ T lymphocyte lines were produced using the mixture of peptides 84-98, 93-107, 90-104 and 19-33 for the stimulation of the autologous dendritic cells, according to a protocol similar to that use for the production of T lymphocyte lines restricted to the set of HLA-DR molecules predominant in the Caucasian population.

d) Analysis of the Specificity of the Lines by ELISPOT

The anti-IFN-γ human monoclonal antibody 1-D1K (MABTECH), diluted to 10 µg/ml in PBS buffer, was adsorbed onto nitrocellulose plates (Multiscreen HA; Millipore) for 1 hour at 37° C. The plates were subsequently washed with PBS and then saturated with complete IMDM medium (100 µl/well), for 1 h at 37° C. The antigen-presenting cells are autologous PBMCs, immature autologous dendritic cells prepared as specified above, or a mouse fibroblast line (line L), transfected with the cDNA encoding one of the HLA-DR or HLA-DP4 molecules to be tested (Yu et al. Hum. Immunol. 1990, 27, 132-135), so as to verify the specificity of the lines with respect to the HLA-DR and HLA-DP4 molecules. The antigen-presenting cells ($10^5$ autologous PBMCs, $3 \times 10^4$ transfected L cells or $2 \times 10^4$ immature autologous dendritic cells) and the CD4+ T lymphocytes to be tested ($10^4$ CD4+ T lymphocytes) were subsequently added to the plates and incubated for 24 h at 37° C., in the presence or absence of a single peptide (2 µg), of a mixture of peptides (2 µg of each peptide) or of a protein (Bir5 or Nef). The proteins (1 µM) are incubated for 4 h at 37° C. in the presence of immature dendritic cells, and then washed. The peptides are added directly to the plates. For the dose-response analyses, the peptides are used at various concentrations ranging from $10^{-5}$ to $10^{-10}$ M. After three successive washes with water, and then with PBS buffer-0.05% Tween and, finally, with PBS alone, 100 µl of biotin-conjugated anti-IFN-γ secondary antibody (7-B6-1-biotin, MABTECH), diluted to 0.25 µg/ml in PBS containing 1% BSA, were added to each well. After incubation for one hour, the plates were washed again and incubated with 100 µl/well of extravidin-phosphatase (E-2636, SIGMA), diluted to 1/6000. After washing of the plates in PBS buffer, 100 µl of NBT/BCIP substrate (B-5655, SIGMA), diluted in water (one tablet in 10 ml of water), were distributed into each well. The immunoenzymatic revelation was stopped after approximately 10 minutes by thorough rinsing of the plates in water, and the colored spots were counted using an automatic reader (ELISPOT reader system, AID). The lines are considered to be positive when the number of spots is greater than three times that obtained with the negative control (control without peptides) with a minimum of 50 spots. The control without presenting cells makes it possible to verify the specificity of the response for HLA-DR or HLA-DP4 (restriction control).

2) Results a) Lines Specific for all the Predominant HLA II Molecules 98 survivin-specific CD4+ T lymphocyte lines were obtained from seven normal donors (table VI). The specificity of the lines for the survivin peptides was analyzed by IFN-γ ELISPOT using autologous PBMCs as antigen-presenting cells.

TABLE VI

Summary of the specificity of the T lymphocyte lines
No. of T lymphocyte lines

| Individual | peptide | | | | | | |
|---|---|---|---|---|---|---|---|
| | 17-31 | 20-34 | 84-98 | 90-104 | 93-107 | 96-110 | 128-142 |
| D169 | 0 | 0 | 0 | 1 | 1 | 12 | 0 |
| D171 | 2 | 1 | 3 | 3 | 0 | 0 | 7 |
| D174 | 10 | 0 | 0 | 3 | 2 | 1 | 1 |
| D179 | 1 | 0 | 2 | 2 | 0 | 2 | 4 |
| D187 | 4 | 6 | 0 | 1 | 0 | 2 | 1 |
| D188 | 1 | 2 | 3 | 7 | 3 | 1 | 0 |
| D180 | 0 | 0 | 3 | 2 | 2 | 1 | 1 |
| Total | 18 | 9 | 11 | 19 | 8 | 19 | 14 |
| Frequency of responders | 5/7 | 3/7 | 4/7 | 7/7 | 4/7 | 6/7 | 5/7 |

FIG. 1 shows the results obtained with 12 CD4+ T lymphocyte lines derived from normal donors 171 and 174. These lines are stimulated with the peptide mixture presented by autologous dendritic cells but in the absence of the mixture. Among the 60 wells seeded for each donor, 12 and 13 peptide-specific T lymphocyte lines were obtained, respectively for donor 171 and donor 174, suggesting that these lines derive from a few T lymphocyte precursors which were amplified by the weekly stimulations with the peptides. In fact, the T lymphocyte lines are generally specific for a single peptide or for two overlapping peptides, suggesting that they are specific for the region common to the two peptides (FIG. 1). All the peptides induced at least one line (table VI and FIG. 1).

The seven donors cover the HLA-DR haplotypes predominant in the population (table VI), namely: HLA-DR1, -DR4, -DR7, -DR1, -DR13 and -DR15 and the corresponding second DR molecule (DRB3, DRB4 and DRB5). Among the HLA-DR molecules predominant in the Caucasian population, only the HLA-DR3 molecule is absent. Five donors have an HLA-DP4 molecule, in accordance with the frequency of this molecule in the Caucasian population. The peptide mixture induces specific CD4+ T lymphocyte lines in each donor, although the donor sampling was selected so as to include multiple HLA II haplotypes. Peptide 17-31 induces 18 T lymphocyte lines, peptide 20-34 induces 9 lines, peptide 84-98 induces 11 lines, peptide 90-104 induces 19 lines, peptide 93-107 induces 8 lines, peptide 96-110 induces 19 lines and peptide 128-142 induces 14 lines. Peptide 90-104 is immunogenic in all the donors and peptides 17-31, 96-110 and 128-142 induced T lymphocyte lines in five or six of the seven donors.

The restriction elements of the HLA II molecules responsible for the specific stimulation of the CD4+ T lymphocytes by the peptides was evaluated for 19 different CD4+ T lymphocyte lines, by IFN-γ ELISPOT, in the presence of L cells transfected with one of the HLA-DR molecules or with the HLA-DP4 molecule, or in the absence of presenting cells. The lines are induced specifically by the presentation of the peptide by the antigen-presenting cells, given that no IFN-γ production is detected in the absence of peptide (FIG. 2) and that a modest stimulation is observed in the absence of presenting cells.

Figure 2:
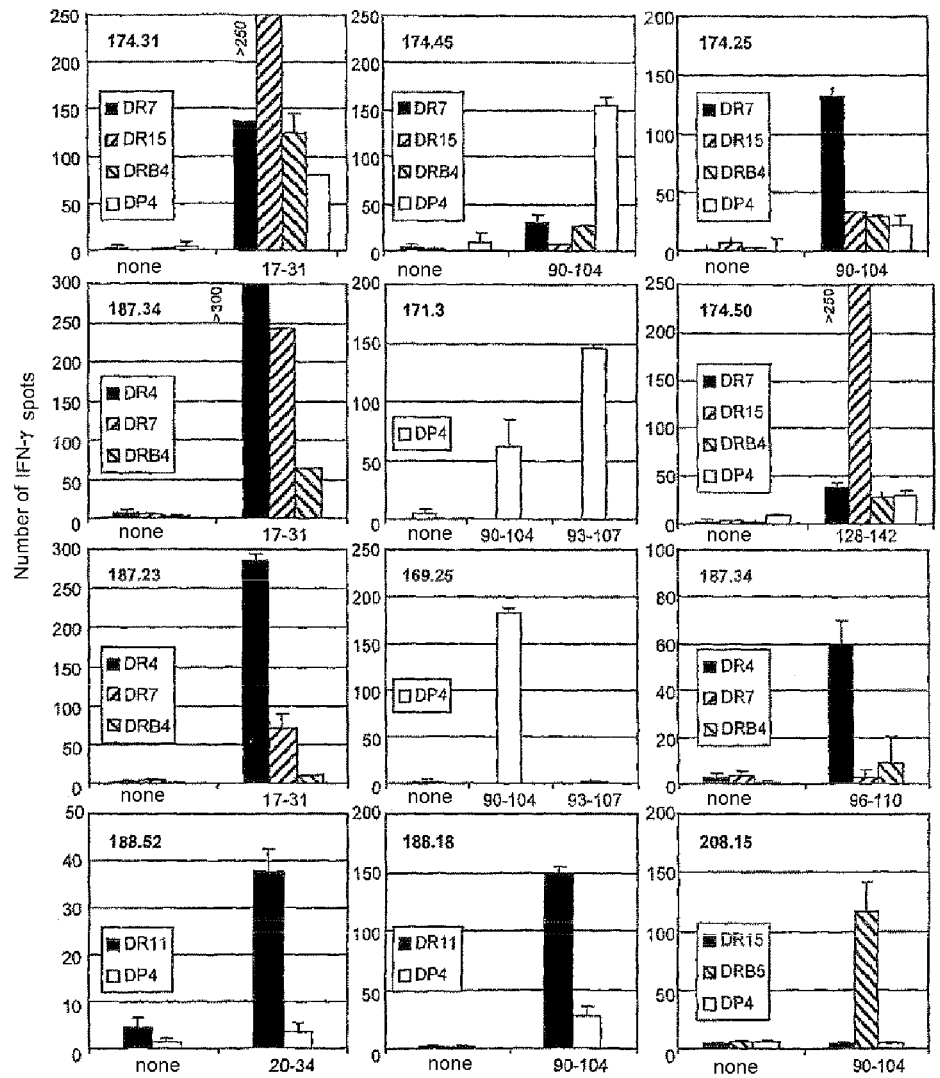
FIG. 2 illustrates the HLA II restriction elements of the CD4+ T lymphocyte lines specific for various survivin peptides, derived from six normal donors (169, 171, 174, 187, 188, 208). The CD4+ T lymphocyte lines were obtained after three stimulations one week apart, with autologous dendritic cells loaded with a mixture of the seven peptides selected (17-31, 20-34, 84-98, 90-104, 93-107, 96-110 and 128-142). The HLA II restriction of the T lymphocyte lines was evaluated by IFN-γ ELISPOT. $10^4$ CD4+ T lymphocytes were incubated, in duplicate, with $3 \times 10^4$ L cells transfected with one of the HLA-DR or HLA-DP4 molecules, in the presence or absence of the appropriate peptide. Each bar represents the mean number of spots of the duplicates±the standard deviation.

FIG. 2 illustrates the results obtained for 12 of the lines tested. Most of the T lymphocyte lines are stimulated by their peptide presented by a single HLA II molecule. However, a degeneration of the recognition is observed, for example for the 174.31 and 187.34 lines. The stimulation does not result from the presentation of the peptides by activated neighboring T lymphocytes, since only a modest stimulation is observed in the absence of L cells. These results show that DR7, DR15, DP4 and DRB4 are restriction elements for peptides 17-31; DP4 is a restriction element for peptide 20-34, DR7, DR11, DRB5 and DP4 are restriction elements for peptide 90-104, DR11 and DP4 are restriction elements for peptide 93-107, DR4, DR7 and DRB4 are restriction elements for peptide 96-110, and DR15 is a restriction element for peptide 128-142.

Figure 3:
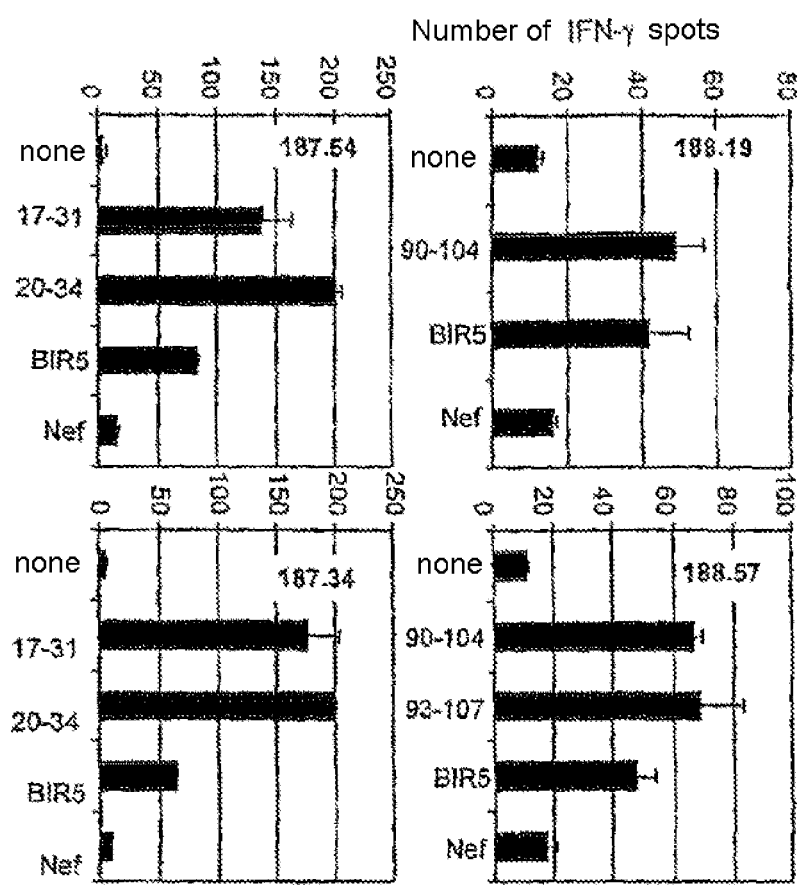
FIG. 3 illustrates the presentation of survivin to the peptide-specific CD4+ T lymphocyte lines. Survivin-specific CD4+ T lymphocyte lines were obtained from PBMCs from two normal donors (187 and 188). Survivin (BIR5) and the HIV Nef protein were incubated for 4 hours with immature autologous dendritic cells. The dendritic cells (DCs) were subsequently washed, and then incubated with the CD4+ T lymphocytes ($2 \times 10^4$ DCs and $10^4$ CD4+ T lymphocytes). The CD4+ T lymphocyte response was measured by IFN-γ ELISPOT. Each bar represents the mean number of spots of the duplicates±the standard deviation.

The ability of seven peptide-specific T lymphocyte lines derived from two different donors, to recognize the native protein was also analyzed. The results given in FIG. 3 are representative of these experiments. The two T lymphocyte lines (187.54 and 187.34) specific for peptides 17-31 and 20-34 specifically recognize the autologous dendritic cells, preloaded with recombinant survivin. They are not stimulated in the presence of dendritic cells that are not loaded or dendritic cells that are loaded with the HIV Nef protein. Similarly, the T lymphocyte lines 188.19 and 188.57 are stimulated by peptides 90-104 and 93-107, alone or as a mixture, and specifically recognize the survivin protein.

Figure 4:
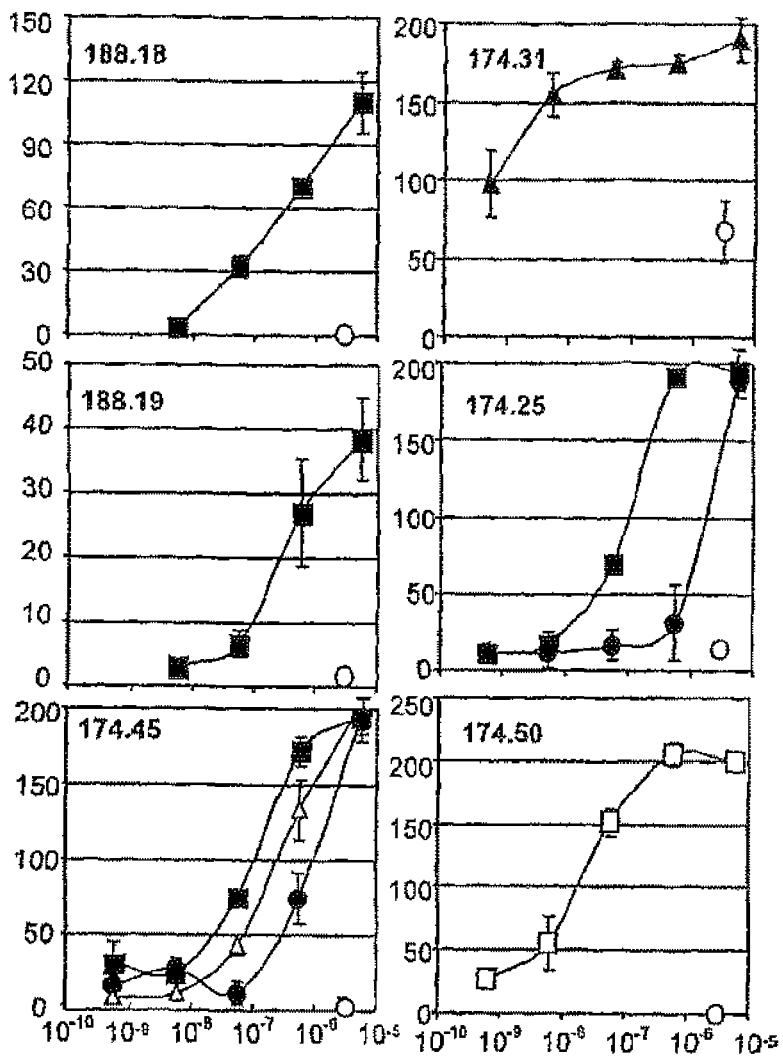
FIG. 4 illustrates the response of the survivin-specific CD4+ T lymphocyte lines to decreasing doses of peptide. Survivin-specific CD4+ T lymphocyte lines were obtained from PBMCs from two normal donors (174 and 188). The lines were incubated with decreasing concentrations ($10^{-5}$ to $10^{-10}$ M) of peptide 17-31 (▲), 90-104 (■), 93-107 (■), 96-110 (Δ) or 128-142 (□), in the presence of $10^5$ autologous PBMCs. The CD4+ T lymphocyte response was measured by IFN-γ ELISPOT.

Finally, the sensitivity of the peptide recognition by the T lymphocytes was evaluated, in the presence of decreasing doses of peptide (FIG. 4). Apart from peptide 93-107, all the peptides stimulate the T lymphocytes and are efficiently recognized by the peptide-specific T lymphocyte lines, at concentrations above $10^{-6}$ M. Peptide 17-31 is particularly effective since it is capable of stimulating autologous CD4+ T lymphocytes at a very low concentration ($10^{-10}$ M).

b) HLA-DP4-Specific Lines

Four HLA-DP4-restricted lines specific for a survivin peptide were demonstrated; these lines are stimulated by the peptide mixture presented by HLA-DP4, but in the absence of the mixture (negative control) or of HLA-DP4 (control without APCs, table VII).

TABLE VII

Immunogenicity of the peptides in an HLA-DP4 context
Number of spots

| Donor | Lines | Negative control | Mixture of peptides | 84-98 | 93-107 | 90-104 | 19-33 | Without APCs |
|---|---|---|---|---|---|---|---|---|
| 169 | 169-14 | 2 (±0) | 210 (±11) | 4 (±2) | 3 (±1) | 182 (±21) | 1 (±0) | 56 (±21) |
| | 169-34 | 4 (±4) | 255 (±18) | 3 (±3) | 2 (±2) | 4 (±2) | 228 (±17) | 10 (±3) |
| | 169-56 | 3 (±1) | 199 (±24) | 2 (±2) | 2 (±2) | 2 (±1) | 195 (±0) | 104 (±30) |
| 171 | 171-3 | 5 (±4) | 103 (±18) | 7 (±1) | 145 (±4) | 62 (±33) | 5 (±0) | 1 (±1) |

Each line responds to one of the peptides of the mixture. Out of the four peptides of the mixture, three are immunogenic in an HLA-DP4 context (peptides 93-107, 90-104 and 19-33).

As emerges from the above, the invention is in no way limited to those of its methods of implementation, execution and application that have just been more explicitly described; on the contrary, it encompasses all the variants thereof that may occur to a person skilled in the art, without departing from either the context or the scope of the present invention.

The invention claimed is:

1. A method of inducing a survivin-specific CD4+ T-cell response in a subject, the method comprising administering a peptide to the subject, the peptide being selected from the group consisting of:
   a) the peptides of 13 to 18 consecutive amino acids located between positions 17 and 34 of SEQ ID NO: 42 which include at least positions 20 to 31,
   b) the peptides of 15 to 30 consecutive amino acids located between positions 84 and 113 of SEQ ID NO: 42 which include at least positions 84 to 98, and the peptides of 13 to 30 consecutive amino acids located between positions 84 and 113 of SEQ ID NO: 42 which include at least positions 93 to 104 or 99 to 110, and
   c) the peptides of 15 to 21 consecutive amino acids located between positions 122 and 142 of SEQ ID NO: 42 which include at least positions 128 to 142,
   said peptides in a), b) or c), having a binding activity of less than 1000 nM to at least three HLA II molecule predominant in the Caucasian population, and being capable of inducing survivin-specific CD4+ T lymphocytes.

2. The method as claimed in claim 1, characterized in that said HLA II molecules predominant in the Caucasian population are selected from the group consisting of: HLA-DR1, HLA-DR3, HLA-DR4, HLA-DR7, HLA-DR11, HLA-DR13, HLA-DR15, HLA-DRB3, HLADRB4, HLA-DRB5 and HLA-DP4.

3. The method as claimed in claim 2, characterized in that said HLA II molecules are encoded, respectively, by the HLA alleles DRBI*0101, DRB1*0301, DRB1*0401, DRB1*0701, DRB1*1101, DRBI*1301, DRB1*1501, DRB3*0101, DRB4*0101, DRB5*0101, DP*0401 and DP*0402.

4. The method as claimed in claim 3, characterized in that it is capable of being presented by at least one HLA-DP401 or HLA-DP402 molecule.

5. The method as claimed in claim 1, characterized in that it is selected from the group consisting of the peptides of 15 amino acids located between the following positions of SEQ ID NO: 42: 17 to 31, 19 to 33, 20 to 34, 84 to 98, 90 to 104, 91 to 105, 93 to 107, 96 to 110, 99 to 113, and 128 to 142.

6. The method as claimed in claim 5, characterized in that it is capable of being presented by at least four HLA II molecules predominant in the Caucasian population, and in that it is selected from the group consisting of the peptides: 17-31, 19-33, 20-34, 84-98, 90-104, 91-105, 93-107, 96-110 and 128-142 of SEQ ID NO: 42.

7. The method as claimed in claim 6, characterized in that it is capable of being presented by an HLA-DP401 or HLA-DP402 molecule, and in that it is selected from the group consisting of the peptides: 17-31, 19-33, 20-34, 84-98, 90-104, 91-105, 93-107 and 96-110 of SEQ ID NO: 42.

8. The method as claimed in claim 5, characterized in that it is selected from the group consisting of the sequences SEQ ID Nos: 5, 6, 7, 17, 19, 20, 21, 23, and 28.

9. The method as claimed in claim 1, characterized in that it has a sequence of 13, 14, 15, 16, 17, 18, 19, 20, 21, 22, 23, 24 or 25 amino acids.

10. The method of claim 1, wherein the peptides is comprised in an immunogenic or vaccinal composition, further comprising a pharmaceutically acceptable carrier, a carrier substance or an adjuvant.

11. The method of claim 10, wherein the immunogenic or vaccinal composition further comprises at least one additional peptide, said additional peptide comprising a survivin CD8+ T epitope, in the form of a mixture of peptides, of a polyepitopic fragment and/or of an expression vector encoding said peptides or said fragment.

12. The method of claim 11, wherein the additional peptide comprising a surviving CD8+ T epitope has an amino acid sequence selected from the group consisting of the sequences SEQ ID Nos: 37 to 39.

13. The method of claim 10, wherein the immunogenic or vaccinal composition comprises at least two different peptides selected from the group consisting of one of the following combinations:
   peptide 17-31 and at least one of peptides 19-33, 90-104 or 128-142,
   peptide 19-33 and peptide 96-110,
   peptide 90-104 and peptide 17-31,
   peptide 96-110 and peptide 90-104, and
   peptides 93-107 and 128-142, and at least one of peptides 17-31, 19-33, 96-110 or 90-104 of SEQ ID NO: 42.

14. The method of claim 10, wherein the immunogenic composition comprises a universal CD4+ T epitope.

15. The method of claim 1, wherein the peptide does not have an amino acid sequence identical to the amino acid sequence of the positions 89 and 101 of SEQ ID NO: 42.

* * * * *

```
                        SEQUENCE LISTING

<160> NUMBER OF SEQ ID NOS: 42

<210> SEQ ID NO 1
<211> LENGTH: 15
<212> TYPE: PRT
<213> ORGANISM: Homo sapiens

<400> SEQUENCE: 1

Met Gly Ala Pro Thr Leu Pro Pro Ala Trp Gln Pro Phe Leu Lys
1               5                   10                  15

<210> SEQ ID NO 2
<211> LENGTH: 15
<212> TYPE: PRT
<213> ORGANISM: Homo sapiens

<400> SEQUENCE: 2

Pro Thr Leu Pro Pro Ala Trp Gln Pro Phe Leu Lys Asp His Arg
1               5                   10                  15

<210> SEQ ID NO 3
<211> LENGTH: 15
<212> TYPE: PRT
<213> ORGANISM: Homo sapiens

<400> SEQUENCE: 3

Pro Ala Trp Gln Pro Phe Leu Lys Asp His Arg Ile Ser Thr Phe
1               5                   10                  15

<210> SEQ ID NO 4
<211> LENGTH: 15
<212> TYPE: PRT
<213> ORGANISM: Homo sapiens

<400> SEQUENCE: 4

Pro Ala Trp Gln Pro Phe Leu Lys Asp His Arg Ile Ser Thr Phe
1               5                   10                  15

<210> SEQ ID NO 5
<211> LENGTH: 15
<212> TYPE: PRT
<213> ORGANISM: Homo sapiens
```

<400> SEQUENCE: 5

His Arg Ile Ser Thr Phe Lys Asn Trp Pro Phe Leu Glu Gly Cys
1               5                   10                  15

<210> SEQ ID NO 6
<211> LENGTH: 15
<212> TYPE: PRT
<213> ORGANISM: Homo sapiens

<400> SEQUENCE: 6

Ile Ser Thr Phe Lys Asn Trp Pro Phe Leu Glu Gly Cys Ala Cys
1               5                   10                  15

<210> SEQ ID NO 7
<211> LENGTH: 15
<212> TYPE: PRT
<213> ORGANISM: Homo sapiens

<400> SEQUENCE: 7

Ser Thr Phe Lys Asn Trp Pro Phe Leu Glu Gly Cys Ala Cys Thr
1               5                   10                  15

<210> SEQ ID NO 8
<211> LENGTH: 15
<212> TYPE: PRT
<213> ORGANISM: Homo sapiens

<400> SEQUENCE: 8

Lys Asn Trp Pro Phe Leu Glu Gly Cys Ala Cys Thr Pro Glu Arg
1               5                   10                  15

<210> SEQ ID NO 9
<211> LENGTH: 15
<212> TYPE: PRT
<213> ORGANISM: Homo sapiens

<400> SEQUENCE: 9

Glu Arg Met Ala Glu Ala Gly Phe Ile His Cys Pro Thr Glu Asn
1               5                   10                  15

<210> SEQ ID NO 10
<211> LENGTH: 15
<212> TYPE: PRT
<213> ORGANISM: Homo sapiens

<400> SEQUENCE: 10

Ala Gly Phe Ile His Cys Pro Thr Glu Asn Glu Pro Asp Leu Ala
1               5                   10                  15

<210> SEQ ID NO 11
<211> LENGTH: 15
<212> TYPE: PRT
<213> ORGANISM: Homo sapiens

<400> SEQUENCE: 11

Pro Asp Leu Ala Gln Cys Phe Phe Cys Phe Lys Glu Leu Glu Gly
1               5                   10                  15

<210> SEQ ID NO 12
<211> LENGTH: 15
<212> TYPE: PRT
<213> ORGANISM: Homo sapiens

```
<400> SEQUENCE: 12

Gln Cys Phe Phe Cys Phe Lys Glu Leu Glu Gly Trp Glu Pro Asp
1               5                   10                  15

<210> SEQ ID NO 13
<211> LENGTH: 15
<212> TYPE: PRT
<213> ORGANISM: Homo sapiens

<400> SEQUENCE: 13

Phe Cys Phe Lys Glu Leu Glu Gly Trp Glu Pro Asp Asp Asp Pro
1               5                   10                  15

<210> SEQ ID NO 14
<211> LENGTH: 15
<212> TYPE: PRT
<213> ORGANISM: Homo sapiens

<400> SEQUENCE: 14

Lys Glu Leu Glu Gly Trp Glu Pro Asp Asp Asp Pro Ile Glu Glu
1               5                   10                  15

<210> SEQ ID NO 15
<211> LENGTH: 15
<212> TYPE: PRT
<213> ORGANISM: Homo sapiens

<400> SEQUENCE: 15

Glu Gly Trp Glu Pro Asp Asp Asp Pro Ile Glu Glu His Lys Lys
1               5                   10                  15

<210> SEQ ID NO 16
<211> LENGTH: 15
<212> TYPE: PRT
<213> ORGANISM: Homo sapiens

<400> SEQUENCE: 16

Asp Pro Ile Glu Glu His Lys Lys His Ser Ser Gly Cys Ala Phe
1               5                   10                  15

<210> SEQ ID NO 17
<211> LENGTH: 15
<212> TYPE: PRT
<213> ORGANISM: Homo sapiens

<400> SEQUENCE: 17

Cys Ala Phe Leu Ser Val Lys Lys Gln Phe Glu Glu Leu Thr Leu
1               5                   10                  15

<210> SEQ ID NO 18
<211> LENGTH: 15
<212> TYPE: PRT
<213> ORGANISM: Homo sapiens

<400> SEQUENCE: 18

Leu Ser Val Lys Lys Gln Phe Glu Glu Leu Thr Leu Gly Glu Phe
1               5                   10                  15

<210> SEQ ID NO 19
<211> LENGTH: 15
<212> TYPE: PRT
<213> ORGANISM: Homo sapiens
```

-continued

<400> SEQUENCE: 19

Lys Lys Gln Phe Glu Glu Leu Thr Leu Gly Glu Phe Leu Lys Leu
1               5                   10                  15

<210> SEQ ID NO 20
<211> LENGTH: 15
<212> TYPE: PRT
<213> ORGANISM: Homo sapiens

<400> SEQUENCE: 20

Lys Gln Phe Glu Glu Leu Thr Leu Gly Glu Phe Leu Lys Leu Asp
1               5                   10                  15

<210> SEQ ID NO 21
<211> LENGTH: 15
<212> TYPE: PRT
<213> ORGANISM: Homo sapiens

<400> SEQUENCE: 21

Phe Glu Glu Leu Thr Leu Gly Glu Phe Leu Lys Leu Asp Arg Glu
1               5                   10                  15

<210> SEQ ID NO 22
<211> LENGTH: 15
<212> TYPE: PRT
<213> ORGANISM: Homo sapiens

<400> SEQUENCE: 22

Glu Glu Leu Thr Leu Gly Glu Phe Leu Lys Leu Asp Arg Glu Arg
1               5                   10                  15

<210> SEQ ID NO 23
<211> LENGTH: 15
<212> TYPE: PRT
<213> ORGANISM: Homo sapiens

<400> SEQUENCE: 23

Leu Thr Leu Gly Glu Phe Leu Lys Leu Asp Arg Glu Arg Ala Lys
1               5                   10                  15

<210> SEQ ID NO 24
<211> LENGTH: 15
<212> TYPE: PRT
<213> ORGANISM: Homo sapiens

<400> SEQUENCE: 24

Gly Glu Phe Leu Lys Leu Asp Arg Glu Arg Ala Lys Asn Lys Ile
1               5                   10                  15

<210> SEQ ID NO 25
<211> LENGTH: 15
<212> TYPE: PRT
<213> ORGANISM: Homo sapiens

<400> SEQUENCE: 25

Leu Lys Leu Asp Arg Glu Arg Ala Lys Asn Lys Ile Ala Lys Glu
1               5                   10                  15

<210> SEQ ID NO 26
<211> LENGTH: 15
<212> TYPE: PRT
<213> ORGANISM: Homo sapiens

```
<400> SEQUENCE: 26

Asn Lys Ile Ala Lys Glu Thr Asn Asn Lys Lys Lys Glu Phe Glu
1               5                   10                  15

<210> SEQ ID NO 27
<211> LENGTH: 15
<212> TYPE: PRT
<213> ORGANISM: Homo sapiens

<400> SEQUENCE: 27

Lys Glu Phe Glu Glu Thr Ala Lys Lys Val Arg Arg Ala Ile Glu
1               5                   10                  15

<210> SEQ ID NO 28
<211> LENGTH: 15
<212> TYPE: PRT
<213> ORGANISM: Homo sapiens

<400> SEQUENCE: 28

Ala Lys Lys Val Arg Arg Ala Ile Glu Gln Leu Ala Ala Met Asp
1               5                   10                  15

<210> SEQ ID NO 29
<211> LENGTH: 13
<212> TYPE: PRT
<213> ORGANISM: ARTIFICIAL SEQUENCE
<220> FEATURE:
<223> OTHER INFORMATION: HA 306-318

<400> SEQUENCE: 29

Pro Lys Tyr Val Lys Gln Asn Thr Leu Lys Leu Ala Thr
1               5                   10

<210> SEQ ID NO 30
<211> LENGTH: 15
<212> TYPE: PRT
<213> ORGANISM: artificial sequence
<220> FEATURE:
<223> OTHER INFORMATION: A3 152-166

<400> SEQUENCE: 30

Glu Ala Glu Gln Leu Arg Ala Tyr Leu Asp Gly Thr Gly Val Glu
1               5                   10                  15

<210> SEQ ID NO 31
<211> LENGTH: 15
<212> TYPE: PRT
<213> ORGANISM: artificial sequence
<220> FEATURE:
<223> OTHER INFORMATION: MT 2-16

<400> SEQUENCE: 31

Ala Lys Thr Ile Ala Tyr Asp Glu Glu Ala Arg Arg Gly Leu Glu
1               5                   10                  15

<210> SEQ ID NO 32
<211> LENGTH: 16
<212> TYPE: PRT
<213> ORGANISM: artificial sequence
<220> FEATURE:
<223> OTHER INFORMATION: B1 21-36

<400> SEQUENCE: 32

Thr Glu Arg Val Arg Leu Val Thr Arg His Ile Tyr Asn Arg Glu Glu
1               5                   10                  15
```

<210> SEQ ID NO 33
<211> LENGTH: 13
<212> TYPE: PRT
<213> ORGANISM: artificial sequence
<220> FEATURE:
<223> OTHER INFORMATION: YKL

<400> SEQUENCE: 33

Ala Ala Tyr Ala Ala Ala Lys Ala Ala Ala Leu Ala Ala
1               5                   10

<210> SEQ ID NO 34
<211> LENGTH: 20
<212> TYPE: PRT
<213> ORGANISM: artificial sequence
<220> FEATURE:
<223> OTHER INFORMATION: LOL 191-210

<400> SEQUENCE: 34

Glu Ser Trp Gly Ala Val Trp Arg Ile Asp Thr Pro Asp Lys Leu Thr
1               5                   10                  15

Gly Pro Phe Thr
            20

<210> SEQ ID NO 35
<211> LENGTH: 14
<212> TYPE: PRT
<213> ORGANISM: artificial sequence
<220> FEATURE:
<223> OTHER INFORMATION: E2/E168

<400> SEQUENCE: 35

Ala Gly Asp Leu Leu Ala Ile Glu Thr Asp Lys Ala Thr Ile
1               5                   10

<210> SEQ ID NO 36
<211> LENGTH: 17
<212> TYPE: PRT
<213> ORGANISM: artificial sequence
<220> FEATURE:
<223> OTHER INFORMATION: Oxy 271-287

<400> SEQUENCE: 36

Glu Lys Lys Tyr Phe Ala Ala Thr Gln Phe Glu Pro Leu Ala Ala Arg
1               5                   10                  15

Leu

<210> SEQ ID NO 37
<211> LENGTH: 8
<212> TYPE: PRT
<213> ORGANISM: Homo sapiens

<400> SEQUENCE: 37

Leu Thr Leu Gly Glu Phe Leu Lys
1               5

<210> SEQ ID NO 38
<211> LENGTH: 9
<212> TYPE: PRT
<213> ORGANISM: Homo sapiens

<400> SEQUENCE: 38

Leu Thr Leu Gly Glu Phe Leu Lys Leu
1               5

```
<210> SEQ ID NO 39
<211> LENGTH: 9
<212> TYPE: PRT
<213> ORGANISM: Homo sapiens

<400> SEQUENCE: 39

Ala Tyr Ala Cys Asn Thr Ser Thr Leu
1               5

<210> SEQ ID NO 40
<211> LENGTH: 24
<212> TYPE: PRT
<213> ORGANISM: Homo sapiens

<400> SEQUENCE: 40

Ile Gly Pro Gly Thr Val Ala Tyr Ala Cys Asn Thr Ser Thr Leu Gly
1               5                   10                  15

Gly Arg Gly Gly Arg Ile Thr Arg
            20

<210> SEQ ID NO 41
<211> LENGTH: 11
<212> TYPE: PRT
<213> ORGANISM: artificial sequence
<220> FEATURE:
<223> OTHER INFORMATION: PADRE
<220> FEATURE:
<221> NAME/KEY: misc_feature
<222> LOCATION: (2)..(2)
<223> OTHER INFORMATION: Xaa can be any naturally occurring amino acid

<400> SEQUENCE: 41

Lys Xaa Val Ala Ala Trp Thr Leu Lys Ala Ala
1               5                   10

<210> SEQ ID NO 42
<211> LENGTH: 142
<212> TYPE: PRT
<213> ORGANISM: Homo sapiens

<400> SEQUENCE: 42

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asp Pro Ile Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
        130                 135                 140
```